US009613520B2

(12) United States Patent
Chan et al.

(10) Patent No.: US 9,613,520 B2
(45) Date of Patent: *Apr. 4, 2017

(54) REAL-TIME EVENT COMMUNICATION AND MANAGEMENT SYSTEM, METHOD AND COMPUTER PROGRAM PRODUCT

(71) Applicant: Iodine Software, LLC, Austin, TX (US)

(72) Inventors: William Chan, Austin, TX (US); Michael Kadyan, Austin, TX (US); Joshua Toub, Austin, TX (US); W. Lance Eason, Austin, TX (US)

(73) Assignee: Iodine Software, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/745,886

(22) Filed: Jun. 22, 2015

(65) Prior Publication Data

US 2015/0287317 A1 Oct. 8, 2015

Related U.S. Application Data

(63) Continuation of application No. 13/921,647, filed on Jun. 19, 2013, now Pat. No. 9,092,964.

(Continued)

(51) Int. Cl.
*G08B 1/08* (2006.01)
*G08B 25/01* (2006.01)
*G08B 21/02* (2006.01)

(52) U.S. Cl.
CPC ........... *G08B 25/016* (2013.01); *G08B 21/02* (2013.01)

(58) Field of Classification Search
CPC ....... A61B 5/0002; A61B 5/0022; A61B 5/72; A61B 5/7475; G06F 19/322;
(Continued)

(56) References Cited

U.S. PATENT DOCUMENTS 7,698,366 B2  4/2010  Schofield et al.
9,092,964 B1 *  7/2015  Chan ..................... G08B 21/02
(Continued)

OTHER PUBLICATIONS

Office Action issued for U.S. Appl. No. 13/921,647, mailed Nov. 20, 2014, 8 pages.
Notice of Allowance for U.S. Appl. No. 13/921,647, mailed Apr. 3, 2015, 5 pgs.

*Primary Examiner* — Daniel Previl
(74) *Attorney, Agent, or Firm* — Sprinkle IP Law Group

(57) ABSTRACT

A real time medical communication system for sending Notifications of medical Alerts includes a data translation layer for receiving real time medical data from one or more sources via a network and an Alerts engine. The Alerts engine may include a message processing module including an entity extraction module configured to extract entities from the real time medical data; and a fragment generation module configured to define fragments comprising events of interest for defining one or more medical Alerts. The Alerts engine may further include an Alert generation module that may include fragment query and evaluation modules for analyzing received real time medical data for defined fragments and generating one or more medical Alerts therefrom. A Notification module may also be provided for sending Notifications of Alerts to users.

21 Claims, 28 Drawing Sheets

Related U.S. Application Data

(60) Provisional application No. 61/661,762, filed on Jun. 19, 2012.

(58) Field of Classification Search
CPC . G06F 19/3406; G06F 19/3418; G06Q 50/22; H04L 67/10; G08B 25/016; G08B 21/02
USPC .......... 340/539.12, 527, 534, 538.12, 539.1, 340/568.1, 636.11, 5.32, 5.52, 5.53, 7.55, 340/7.58, 7.59, 815.45
See application file for complete search history.

(56) References Cited

U.S. PATENT DOCUMENTS

| | | | |
|---|---|---|---|
| 2002/0016719 | A1 | 2/2002 | Nemeth et al. |
| 2004/0210488 | A1* | 10/2004 | Doherty .............. G06F 19/3462 705/22 |
| 2008/0172249 | A1 | 7/2008 | Glaser-Seidnitzer et al. |
| 2009/0296540 | A1* | 12/2009 | Gilbert .................... G06F 13/00 369/30.23 |
| 2010/0217623 | A1 | 8/2010 | Schoenberg et al. |
| 2011/0213620 | A1* | 9/2011 | Dziubinski ........... G06F 19/322 705/2 |
| 2013/0223617 | A1 | 8/2013 | Steiner et al. |
| 2014/0316804 | A1* | 10/2014 | Tran ................... G06Q 10/1097 705/2 |
| 2016/0012195 | A1* | 1/2016 | Lee ........................ G06Q 50/24 705/3 |

\* cited by examiner

REAL-TIME EVENT COMMUNICATION AND MANAGEMENT SYSTEM, METHOD AND COMPUTER PROGRAM PRODUCT

CROSS REFERENCE TO RELATED APPLICATIONS

This application is a continuation of, and claims a benefit of priority under 35 U.S.C. 120 of the filing date of U.S. patent application Ser. No. 13/921,647, filed Jun. 19, 2013, entitled "REAL-TIME EVENT COMMUNICATION AND MANAGEMENT SYSTEM, METHOD AND COMPUTER PROGRAM PRODUCT," which claims priority from U.S. Provisional Application No. 61/661,762, filed Jun. 19, 2012, both of which are fully incorporated by reference herein for all purposes.

NOTICE OF COPYRIGHT

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This disclosure relates generally to electronic communications. More particularly, embodiments disclosed herein relate to a system, method, and computer program product for the real-time identification of healthcare events and the contemporaneous creation of caregiver groups for managing those events.

BACKGROUND OF THE RELATED ART

Due to the significant amount of data flowing through a healthcare facility, manual interpretation of the data to determine possible anomalous or outlier events is humanly impossible. By collecting and interpreting such data, a software system can detect anomalous events, such as fever, etc., that may require attention by one or more caregivers. Once an event is detected, the appropriate personnel must be notified of the event for remedial actions to be taken. Because modern caregiving is both a group and specialized activity with many parties that may be 'on' or 'off' call at the time of the event, determining the appropriate personnel to address the event is a challenge. Once the persons are identified, they need to collaborate to resolve the event. Electronic tools that deliver sufficient information and provide the means of resolution for the event must be made available to the identified group of caregivers so that they can resolve the issue in a timely fashion.

Existing solutions have attempted to address the different facets of the problem separately. Electronic tools are available to identify potential events. However, these identification tools tend to cast a wide net, or have decision criteria that are insufficiently specific, leading to identification of events that may not be relevant to a particular patient. When an event is identified, the task of identifying whether the occurrence of the event requires remediation or treatment is typically manual. The person identifying the event may call around to determine the appropriate primary caregiver to address the event. It becomes the primary caregiver's responsibility to interact with other caregivers associated with patient to determine the best course of action to resolve the event. This interaction is also manual and may involve phone calls, paging, text messaging, email or face-to-face conversations.

Advances in information technology continue to bring challenges to healthcare management. Consequently, there is always room for innovations and improvements.

SUMMARY OF THE DISCLOSURE

A real time medical communication system for sending Notifications of medical Alerts, in accordance with embodiments, includes a data translation layer for receiving real time medical data from one or more sources via a network and an Alerts engine. The Alerts engine may be configured to define fragments comprising events of interest for defining one or more medical Alerts. The Alerts engine may further include an Alert generation module that may include fragment query and evaluation modules for analyzing received real time medical data for defined fragments and generating one or more medical Alerts therefrom. A Notification module may also be provided for sending Notifications of Alerts to users. The Alerts and Notifications are user-configurable on a patient-by-patient and/or caregiver-by-caregiver basis.

A real time medical communication method for generating Notifications of medical Alerts, includes receiving real time medical data from one or more sources via a network; defining fragments comprising events of interest for defining one or more medical Alerts; analyzing received real time medical data for defined fragments and generating one or more medical Alerts therefrom; and sending Notifications of Alerts to users. In some embodiments, the Alerts and Notifications are user-configurable on a patient-by-patient and/or caregiver-by-caregiver basis.

A computer program product in accordance with embodiments includes one or more nontransitory machine readable media instructions for implementing a real time medical communication system for generating Notifications of medical Alerts, the instructions for: receiving real time medical data from one or more sources via a network; and defining fragments comprising events of interest for defining one or more medical Alerts; and analyzing received real time medical data for defined fragments and generating one or more medical Alerts therefrom; and sending Notifications of Alerts to users. In some embodiments, the Alerts and Notifications are user-configurable on a patient-by-patient and/or caregiver-by-caregiver basis.

These, and other, aspects of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions and/or rearrangements may be made within the scope of the disclosure without departing from the spirit thereof, and the disclosure includes all such substitutions, modifications, additions and/or rearrangements.

BRIEF DESCRIPTION OF THE DRAWINGS

The drawings accompanying and forming part of this specification are included to depict certain aspects of the disclosure. It should be noted that the features illustrated in the drawings are not necessarily drawn to scale. A more complete understanding of the disclosure and the advantages thereof may be acquired by referring to the following description, taken in conjunction with the accompanying drawings in which like reference numbers indicate like features and wherein.

DETAILED DESCRIPTION

Figure 1:
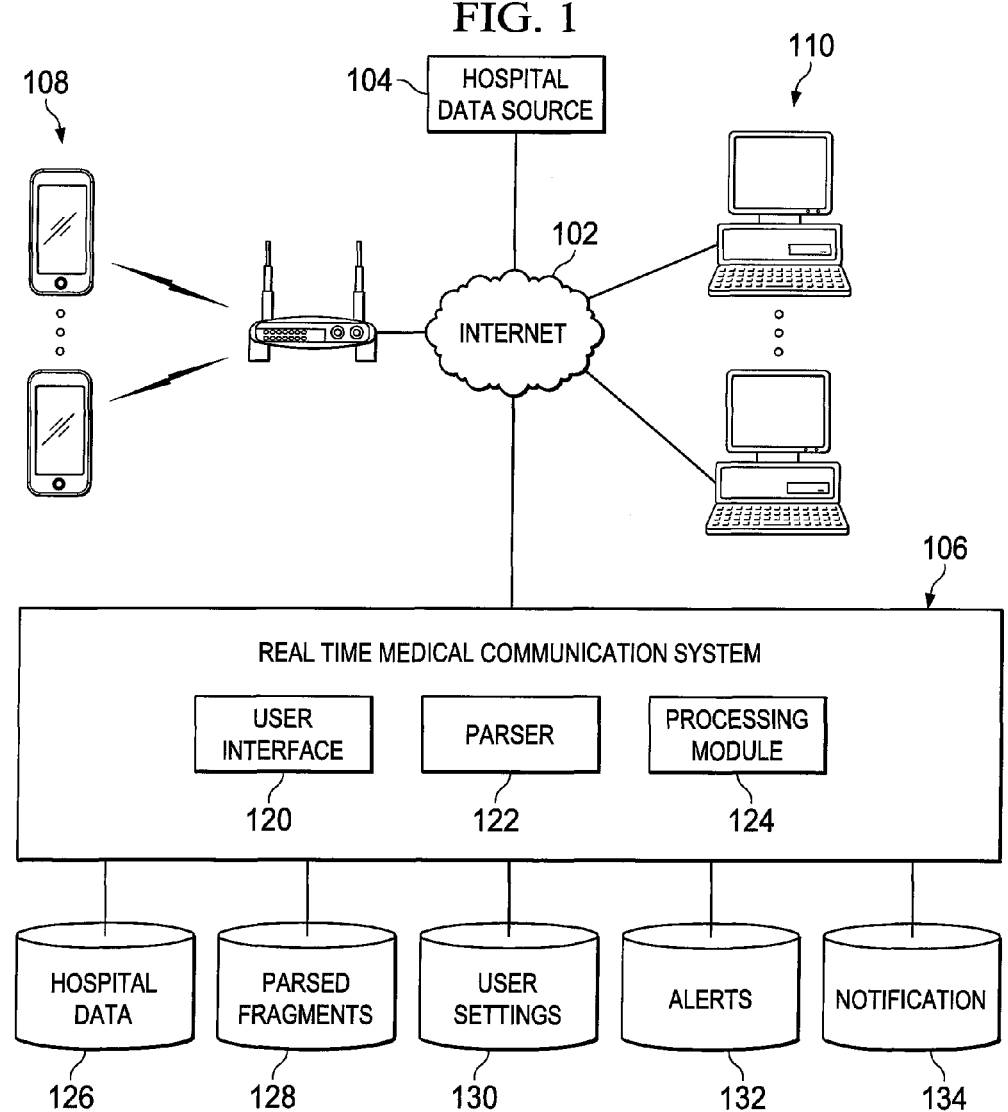
FIG. 1 depicts a diagrammatic representation of a high level network architecture in which embodiments disclosed herein may be implemented.

The disclosure and various features and advantageous details thereof are explained more fully with reference to the exemplary, and therefore non-limiting, embodiments illustrated in the accompanying drawings and detailed in the following description. It should be understood, however, that the detailed description and the specific examples, while indicating the preferred embodiments, are given by way of illustration only and not by way of limitation. Descriptions of known programming techniques, computer software, hardware, operating platforms and protocols may be omitted so as not to unnecessarily obscure the disclosure in detail. Various substitutions, modifications, additions and/or rearrangements within the spirit and/or scope of the underlying inventive concept will become apparent to those skilled in the art from this disclosure.

Embodiments disclosed herein relate generally to the field of social networking and exception event handling, specifically in the context of a hospital or healthcare setting using information and data obtained from healthcare electronic systems. In some embodiments, computer software is provided that uses custom-developed algorithms to identify the events that are important to the healthcare facility and its caregivers (also referred to as "users."). To determine the relevant caregiver(s) who should be notified of the event, the software scans the patient's electronic medical record to identify all caregivers, past and present. If the patient had previously been in the healthcare facility, the software also identifies the caregivers from that visit (as they may have relevant information that pertains to the patient's current condition). The software also automatically identifies the caregivers that are currently on and off call, based on data available from the hospital facility. It then provides an environment whereby all the relevant caregivers have access to the details of the patient event. The caregivers are also provided with electronic tools that allow them to communicate with the other caregivers to determine the best course of action to resolve the event.

In addition, a caregiver user may set Alerts and receive Notifications for more than one patient. All Alerts that are triggered for a patient can be viewed by all caregivers for that patient, even if the caregiver did not actively choose to receive the Alert. They can view the list of all Alert activity with respect to that patient. In one embodiment, this can be implemented as an active stream of information pertaining to a patient. In one embodiment, an active stream of information pertaining to a patient is referred to as a patient care stream. A caregiver can view all the patient care streams for all the patients of which the care giver is involved in their care. The patient care stream allows a user to keep tabs on the patient and to know what other care givers are concerned about or acting on, even if they themselves did not request the Alert. In some embodiments, a patient care stream can be implemented as a dynamic bulletin board, wall, or page with continuously updated information about a particular patient.

In some embodiments, users can define one or more Alert criteria pertaining to one or more patients and medical conditions. Distinct users can request to be Alerted for the same condition for the same patient (e.g., white blood cell count), but with distinct thresholds respectively. In each case, the user can dynamically request a Notification of an Alert when the condition reaches the particular threshold. If a user does want to be notified of a particular Alert, the user can log in to the system and view the Alert.

In some embodiments, the Alerts can be sent to groups of associated users. For example, a medical team may wish to receive Notifications of a first set of criteria while a second team may wish to receive Notifications for a second set of criteria.

In general, embodiments receive real time medical data; extract entities from the real time medical data; and identify events of potential medical interest from the real time medical data. Further, embodiments can employ general configuration, caregiver specific settings, patient specific settings, and patient medical record data to determine caregivers who should be alerted to those events of interest and generating corresponding medical alerts. Finally, notifications of alerts may be sent to caregivers.

Embodiments disclosed herein can provide many advantages. For example, some embodiments remove all the manual processes required to identify the event. With the amount of data regarding patients in a healthcare facility, it is practically impossible to manually filter all the information required to determine the validity of a patient event. The software also makes the task of identifying the relevant caregivers very efficient.

An immediate value brought upon by embodiments is the significant time savings in identifying the event, the relevant caregivers and the efficiency surrounding the resolution of the event. Additional value is then obtained through better care provided to the patient. This has the effect of better quality results for the healthcare facility and better financial utilization through more timely and effective caregiving.

FIG. 1 illustrates an exemplary environment in which real time Notification of medical events may be implemented. In the example illustrated, the system 100 includes a network 102, such as the Internet, one or more real time medical communication (RTMC) systems 106, one or more hospital data sources 104, and one or more user devices 108, 110.

As will be explained in greater detail below, the RTMC 106 may implement one or more servers, such as web servers, for communicating with user devices 108, 110. The user devices 108, 110 may be provided with appropriate interfaces for bi-directionally communicating with the RTMC 106 using web pages, or via email or text messaging, etc.

The RTMC 106 may further include one or more user interfaces 120 for communicating with user devices 108, 110; one or more parsers for receiving data from the one or more hospital data sources 104, and one or more processing modules 124 for implementing various processes discussed herein. In addition, the RTMC 106 may include or be in communication with one or more databases 126-134, as will be discussed in greater detail below.

The user devices 108 may comprise mobile communication devices, such as cellular telephones, smartphones, tablet computers, and the like. Examples include the Apple iPhone, iPad, or cellular telephones running the Android operating system. User devices 110 may include wired or wireless desktop or laptop computer devices, etc.

The user devices 108, 110 may include includes a central processing unit ("CPU", read-only memory ("ROM"), random access memory ("RAM"), a hard drive ("HD") or storage memory, and input/output device(s) ("I/O"). The I/O devices can include a keyboard, monitor, printer, electronic pointing device (e.g., mouse, trackball, touch pad or screen, digitizer, etc.), or the like.

The RTMC system (and the hospital data sources 104) can include server computers which can include a CPU, ROM, RAM, HD, and I/O similar to corresponding items in the user devices.

The one or more health care or hospital data sources 104 may be associated with one or more hospitals or health care facilities and can receive and store medical data associated with patients, health care providers, treatments, etc. As used herein, the term hospital refers to any healthcare facility, clinic, hospital, office, etc., that provides healthcare information that may be of interest. As will be described in greater detail below, the data may be provided as one or more feeds, such as HL7 (Health Level 7) feeds to the RTMC system 106. The HL7 protocol is an open source protocol promulgated by Health Level Seven International, Ann Arbor, Mich., that defines how various healthcare facilities can communicate with each other. It is noted, however, that feeds using other protocols, such as FTP and HTTP, are also possible.

In general, the feeds may comprise ADT feeds (admits, discharges, and transfers, i.e., information related to the "life cycle" of patients at a facility); Orders (i.e., specific procedures ordered for the patients); one or more lab results (e.g., blood tests, etc.); one or more radiology results (e.g., results of x-rays, magnetic resonant imaging (MRI), computer-assisted tomography (CAT) scans, and the like); results of cardiology exams; pharmacy orders; actual pharmaceutical administration; billing and coding; and other information.

In operation, as will be explained in greater detail below, the RTMC system 106 can receive the feeds, process them into a suitable format, define one or more Alerts therefrom, and define criteria for sending Notifications to users 108, 110 notifying of Alerts. In some embodiments, as will be explained in greater detail below, individual users and/or hospitals or care facilities may define the terms of Alerts and Notifications on a patient-by-patient basis.

In particular, in some embodiments using an HL7 feed, a stream of data is updated when an event at a particular hospital or source is updated. The data is stored in a hospital data database 126 and a parser 122 parses the data from the feed to extract desired information. The information is then stored as parsed fragments in database 128. As will be explained in greater detail below, the RTMC 106 may further store user settings 130, Alerts 132, and Notifications 134. Briefly, user settings 130 are input by a caregiver and indicate which patients and which conditions or events he wishes to be monitored and/or notified of. Alerts 132 are matches to the user settings, and Notifications 134 are Alerts for which Notifications are sent. Thus, caregivers can receive Notifications for individual patients based on that particular caregiver's individualized criteria.

Figure 2:
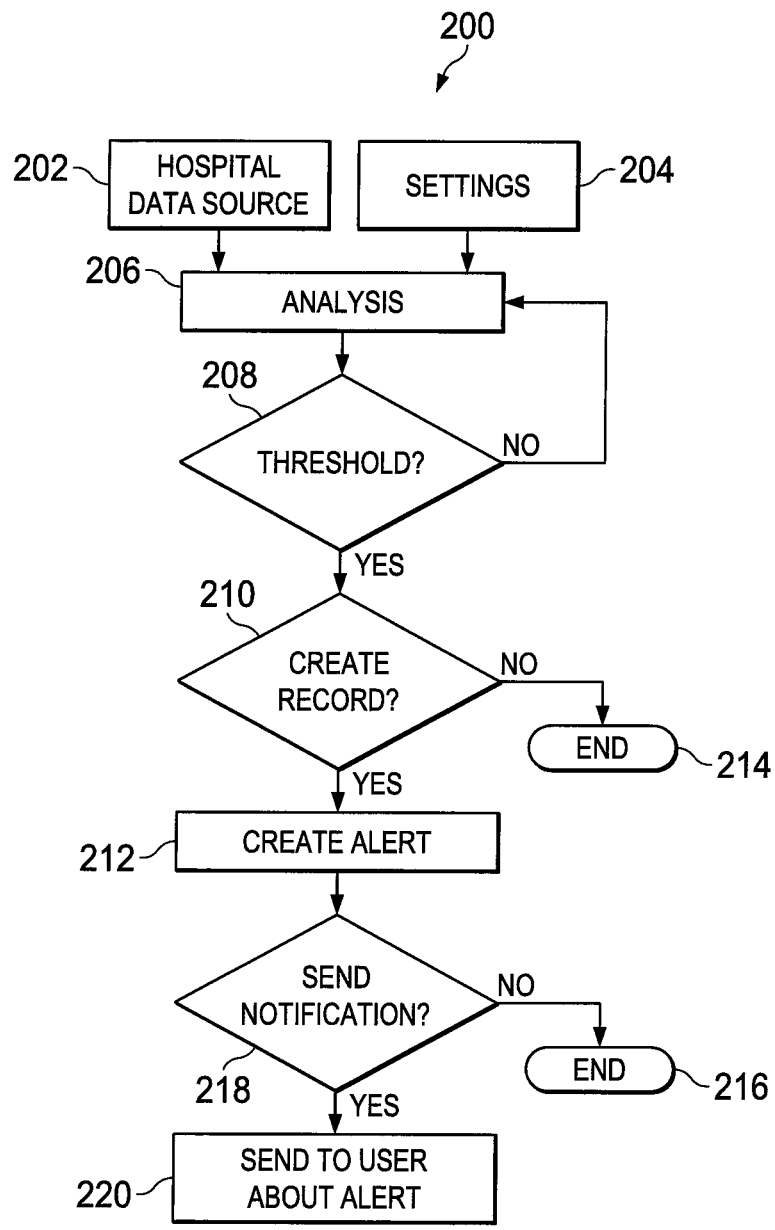
FIG. 2 depicts a diagrammatic representation of exemplary process flow for embodiments disclosed herein.

FIG. 2 illustrates a process flow 200 according to some embodiments as disclosed herein. The RTMC 106 may receive information from the hospital data source(s) (step 202) and from user settings (step 204). As discussed above, in some embodiments, the hospital data source information may come in a variety of forms, such as one or more HL7 feeds, updated on an ongoing basis in real time.

The user settings 204 may be entered via the one or more user devices 108, 110, using suitable graphical user interfaces. These may include, for example, World Wide Web interfaces or application-specific interfaces, such as a smartphone app interface. The user settings 204 may include one or more criteria or dynamically user-selectable thresholds pertaining to medical treatment or conditions, referred to as "events." That is, criteria for event monitoring, as well as creating Alerts and Notifications therefor, may be selectable by the user in real time. In some embodiments, the healthcare facility may itself have one or more settings pertaining to the treatments or conditions.

Such settings may include, for example, particular patients and patient data or events the user wishes to have monitored, as well as combinations thereof; time periods during which the user wishes to receive a Notification; whether or not a record should be made of an event/Alert, etc.

The hospital data source information 202 and the user settings 204 are analyzed by the RTMC 106 (step 206). As will be described in greater detail below, the analysis may include comparing the user settings to the actual real time data received and extracted from the hospital feeds. One or more thresholds pertaining to one or more medical criteria may be analyzed (step 208). This may include, for example, a particular patient's blood pressure or other test result. In some embodiments, a hospital or patient care facility may set a general threshold, while the patient's caregiver may override such a setting on an individual basis. Such a threshold may include, for example, time settings (e.g., it may be less than optimal to notify a caregiver of an event if he is on vacation).

If one or more of the predetermined thresholds are crossed, the RTMC 106 may determine whether an Alert should be made of an event (step 210). In general, an Alert is a record of an event which a caregiver has defined to be of interest. Thus, criteria for making an Alert are based at least in part on user settings 204. If the caregiver has not indicated that an Alert should be created, then the process ends (step 214). Otherwise, an Alert is created and stored in an appropriate database (step 212). In some embodiments, an Alert may comprise a dynamically generated web page associated with an account maintained for the user on the RTMC server(s) and accessible using suitable log in information.

Once the Alert is activated, the RTMC system determines if a Notification should be sent (step 218). Again, the criteria for sending a Notification may be based at least in part on the user settings 204. If no Notification is sent, the process ends (step 216). Otherwise, a Notification is sent to the user who requested the Alert (step 220). In some embodiments, this may include one or more of an email, text message, or telephone message. Typically, the Notification would include some identification of the nature of the Alert and a link to the RTMC web page (not shown) to access the details of the Alert.

As noted above, in some embodiments, users can define one or more alert criteria pertaining to one or more patients and medical conditions. Distinct users can request to be alerted for the same condition for the same patient (e.g., white blood cell count), but with distinct thresholds respectively. For example, user A may define an alert criterion at a first threshold and user B may define a second threshold pertaining to the same medical condition for the same patient. In this case, user A and user B will, if they so choose, receive their notifications based on their respective threshold.

Figure 5:
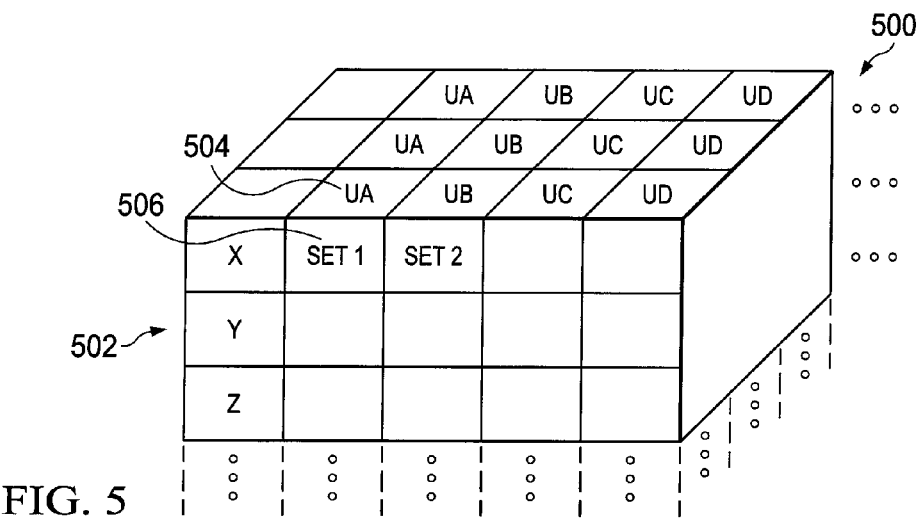
FIG. 5 depicts exemplary data structures which may be used by embodiments disclosed herein.

FIG. 5 depicts an exemplary database structure that may be employed in implementing such embodiments. In particular, database structure 500 shows a plurality of patients X, Y, Z . . . 502 and a plurality of users A, B, C, . . . 504. Each user A, B, C 502 can have a setting 506 for medical condition for each patient X, Y, Z. As a specific example, user A could request a monitoring of patient X's blood pressure and white blood cell count, while user B could request monitoring of patient Y's pulse rate and temperature. User B may also want to be alerted for patient X's blood pressure and white blood cell count at thresholds that are the same or different from those set by user A. Likewise, user A may want to be alerted when and if patient Y's pulse rate and temperature exceed certain thresholds defined by user A. Thus, the settings 506 represent threshold conditions for various conditions. As discussed herein, user A and/or user B may choose to be notified of all or some of such alerts. In each case, the user can dynamically request a notification of an alert when the condition reaches a particular threshold. If a user does want to be notified of a particular alert, the user can log in to the system and view the alert.

As noted above, in some embodiments, users can elect alerts for particular patients based on one or more medical conditions. In some embodiments, the alerts can be sent to groups of associated users. For example, a medical team may wish to receive notifications of a first set of criteria while a second team may wish to receive notifications for a second set of criteria.

Figure 6:
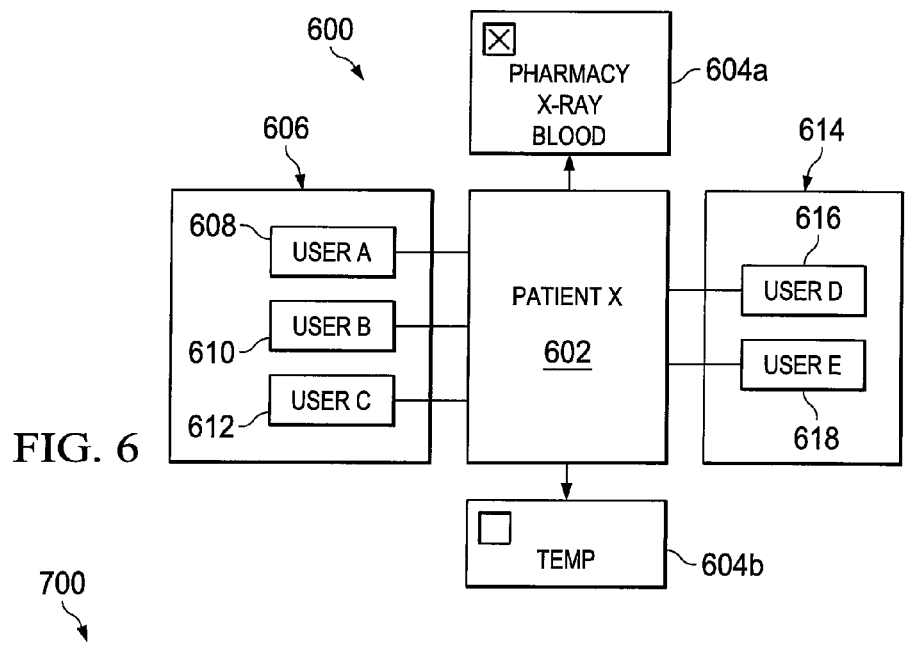
FIG. 6 depicts a diagrammatic representation of a system for implementing embodiments disclosed herein.

This is illustrated by way of example in FIG. 6. As shown, a patient X 602 may be associated with two teams of caregivers 606, 614. Caregivers 606 include User A 608, User B 610, and User C 612. These users may wish to receive notifications based on the patient's pharmaceutical use, x-rays, and blood work (shown at 604a). According to embodiments, they can choose these criteria and thresholds and receive corresponding notifications when alerts are triggered.

Similarly, the users of group 614, User D 616, and User E 618, may wish to receive notification of the patient's temperature (shown at 604b). They can then select a particular threshold temperature to trigger an alert to receive a notification about.

Figure 7:
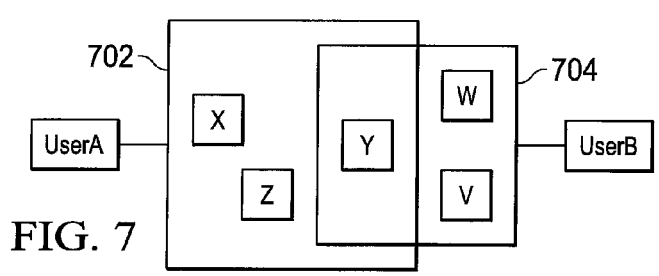
FIG. 7 depicts a diagrammatic representation of a system for implementing embodiments disclosed herein.

In addition, it is noted that in some embodiments, a user may set alerts and receive notifications for more than one patient. This is illustrated more particularly in FIG. 7. Shown at 700 are patient groups 702, 704. Patient group 702 includes patients X, Y, and Z, while patient group 704 includes patients V, W, and Y. User A can elect to set thresholds for alerts for the patients in group 702 while User B can do so for the patients of group 704. In some embodiments, the patient groups can have overlapping memberships.

Operation of embodiments may be illustrated by way of example, as illustrated with reference to FIGS. 3A-3X. More particularly, the example illustrates information that may be displayed for view on a user device 108 as part of a physician's patient care stream 300.

Figure 3A:
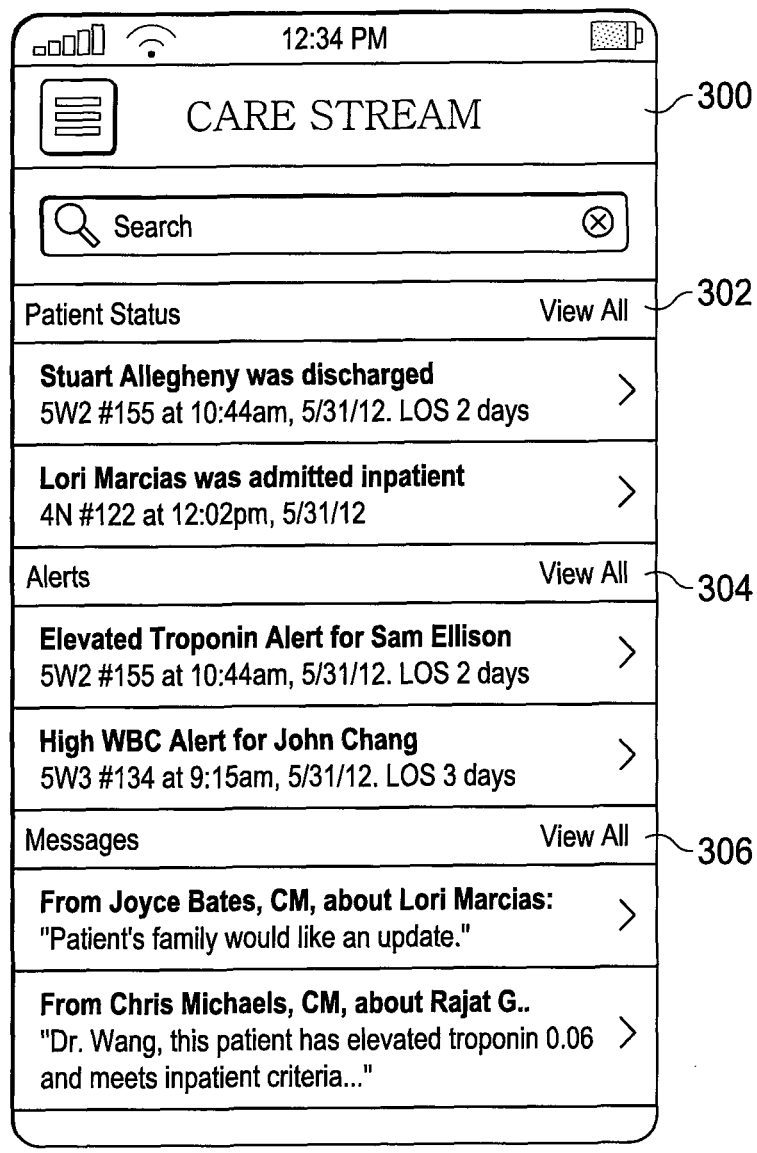
FIG. 3A-FIG. 3X illustrate exemplary user interface screens for interacting with a system in accordance with embodiments disclosed herein.
Figure 3B:
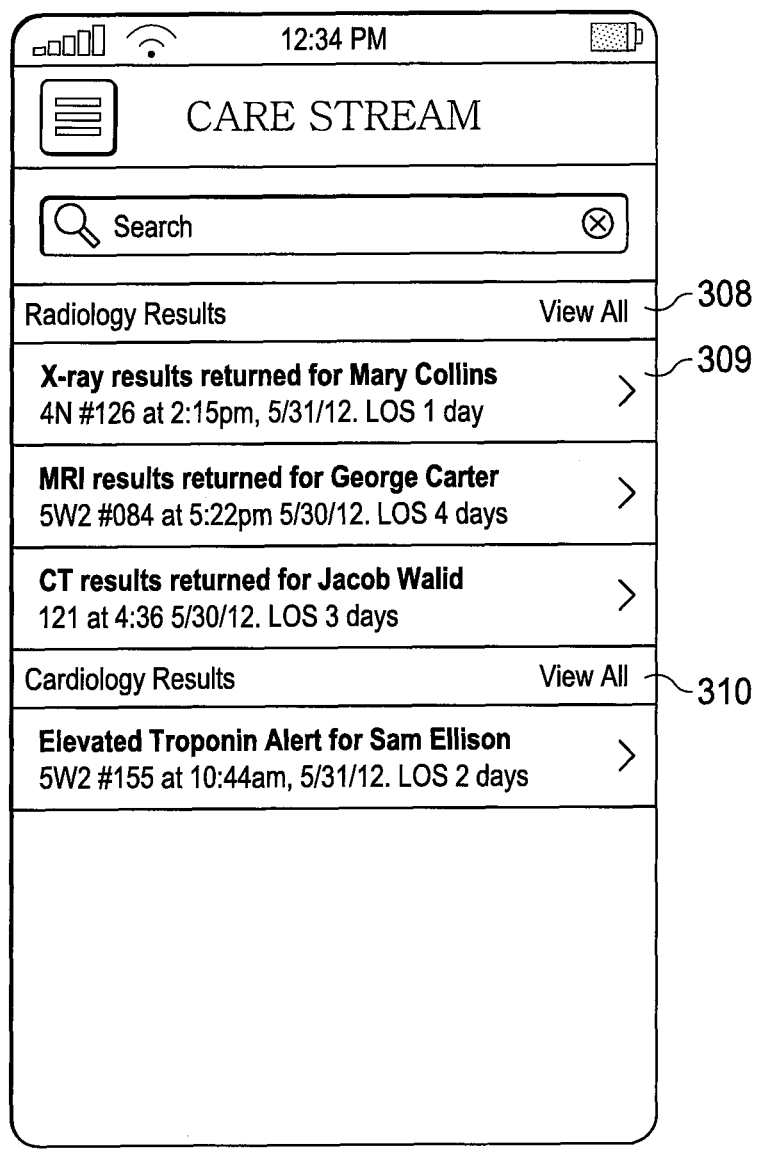

In some embodiments, as shown in FIG. 3A, such a screen can list Patient Status 302, Alerts 304, and Messages 306 for or about the caregiver's patients. As shown in FIG. 3B, example sections in the patient care stream may further include test results such as Radiology Results 308 and Cardiology Results 310. Access to the screen of FIG. 3B may be obtained, for example, by "scrolling" down from the screen of FIG. 3A.

In some embodiments, an icon may be provided for each of the sections delineated. The system may display all the information associated with each topic, with a second page starting from where it is identified on screen.

Figure 3C:
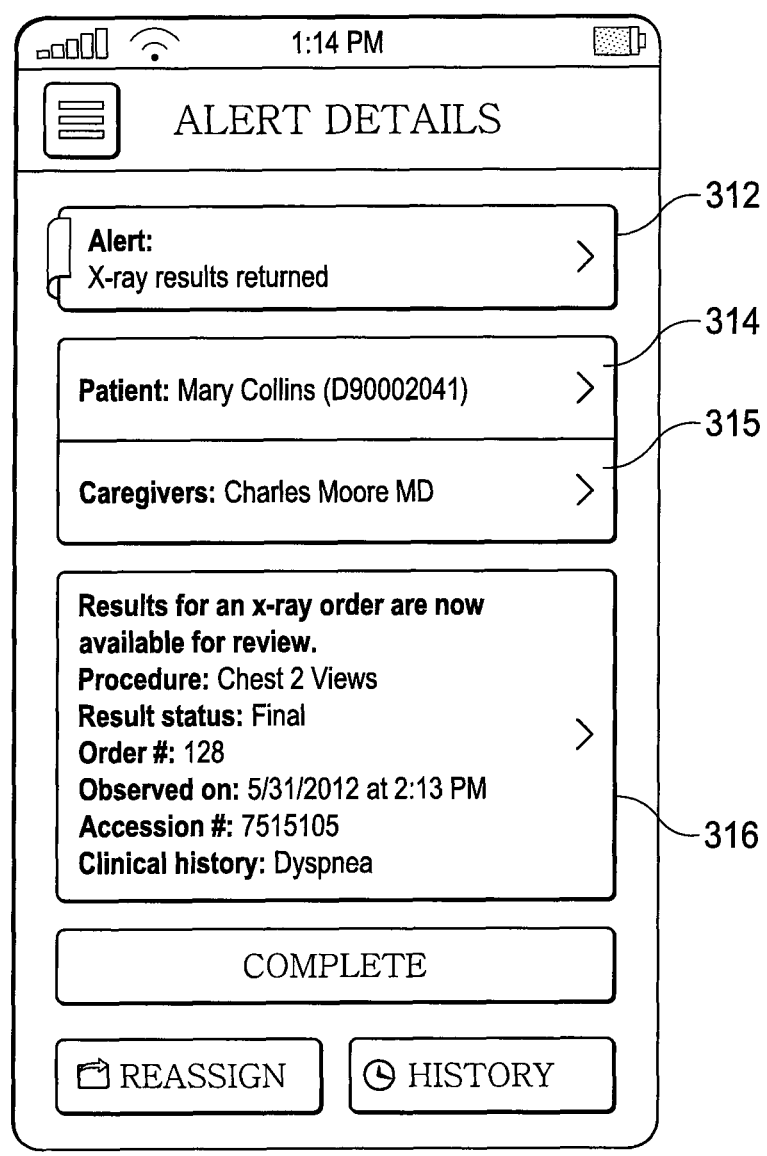
Figure 3D:
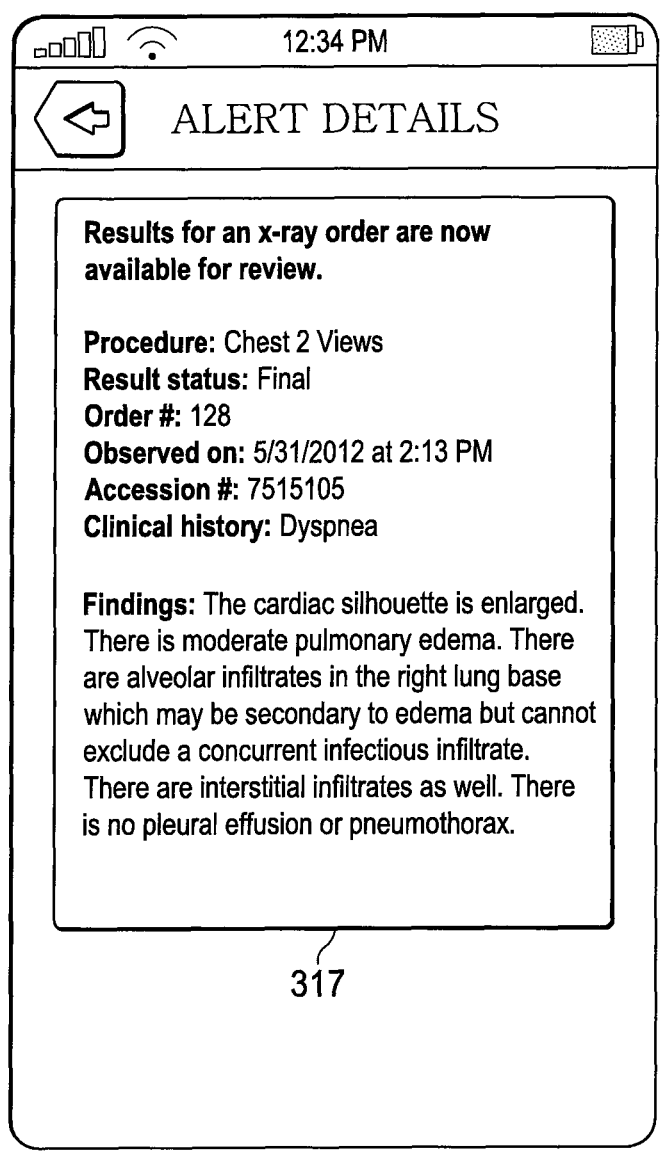

For example, a user can tap on the "X-ray results returned for Mary Collins" item 309 (FIG. 3B) to view the details of the Radiology Result Returned Alert 312 (FIG. 3C). In the example illustrated, the Alert Details include patient and caregiver identifications 314, 315 as well as further information 316 about the Alert. In some embodiments, by tapping on Alert 312, the user can open a new page showing even more expanded details 317 of the particular Alert (FIG. 3D). In some embodiments, as will be explained in greater detail below, a user may reassign an alert by tapping on the Reassign button.

Figure 3E:
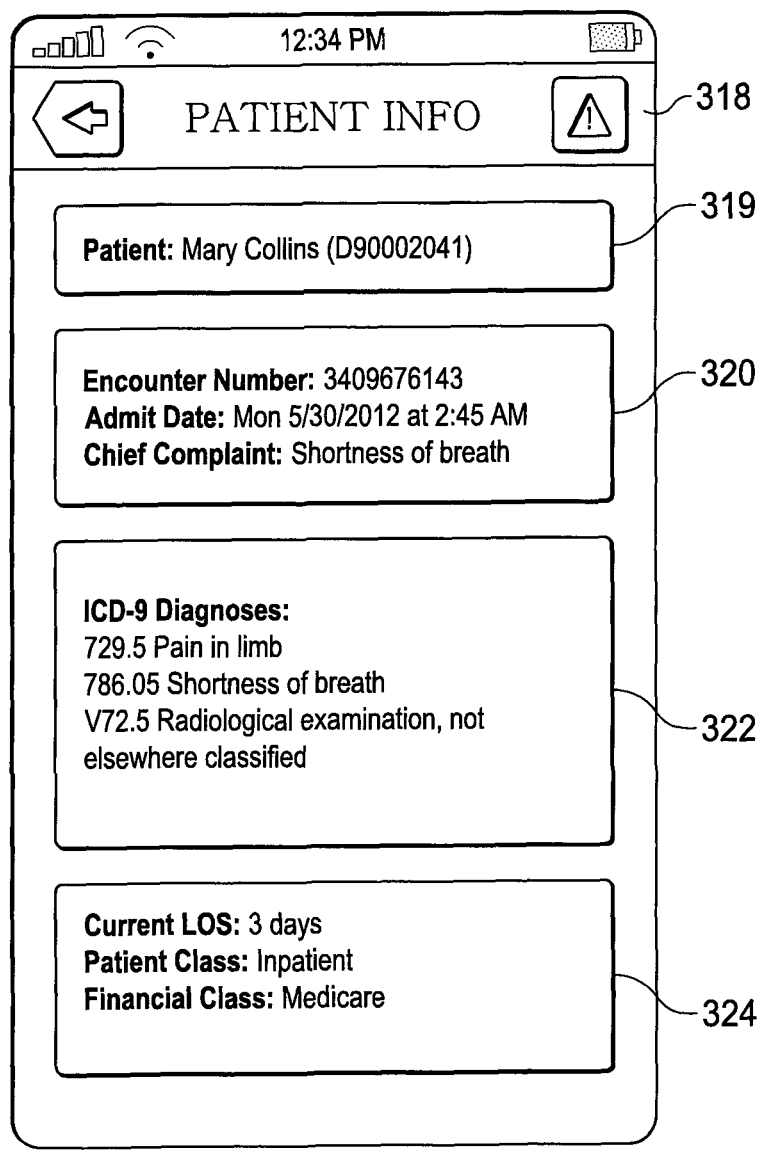

In some embodiments, the user can switch over to the patient information for that Alert by tapping on "Patient" 314 (FIG. 3C). This displays a patient information page 318 as shown in FIG. 3E. In the example illustrated, patient information may include patient name 319, encounter identification 320, diagnosis 322, and hospital stay information 324.

Figure 3F:
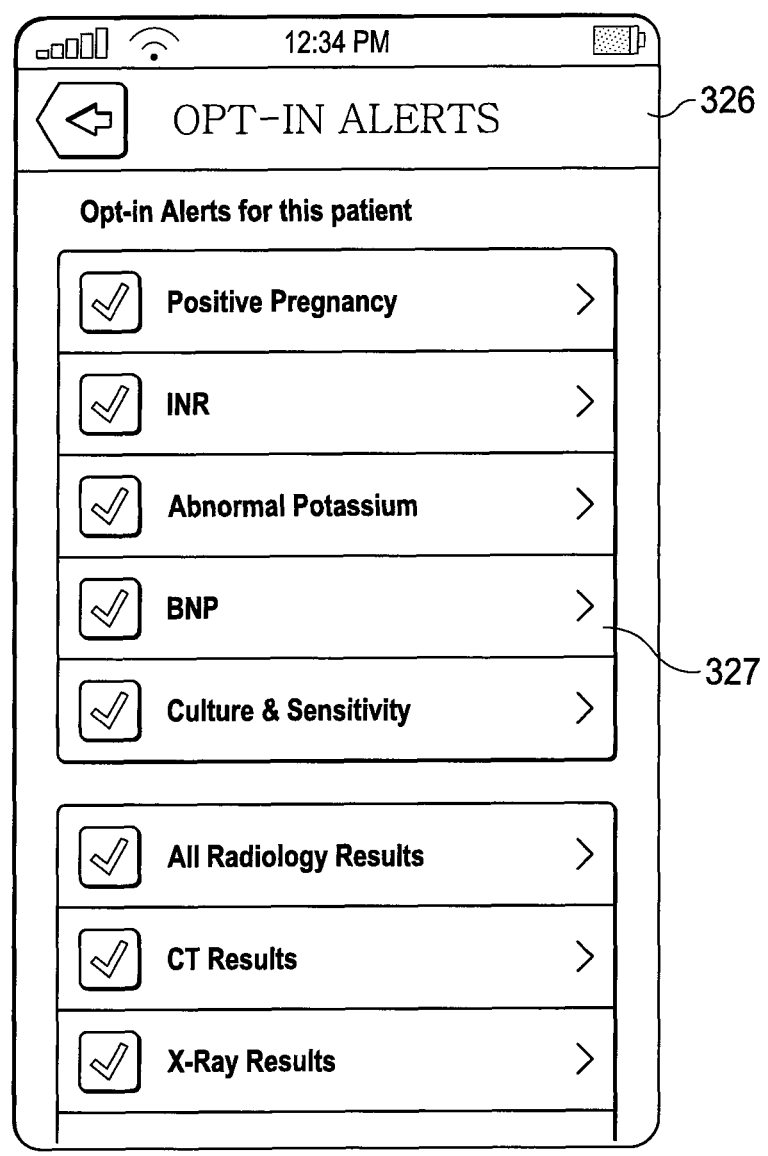

In some embodiments, on the top right of the patient information page 318, there can be a "+" or some other icon (not shown) that allows user to add an Alert. Users can tap on such an icon to see a list of Opt-in Alerts 326 (FIG. 3F).

Figure 3G:
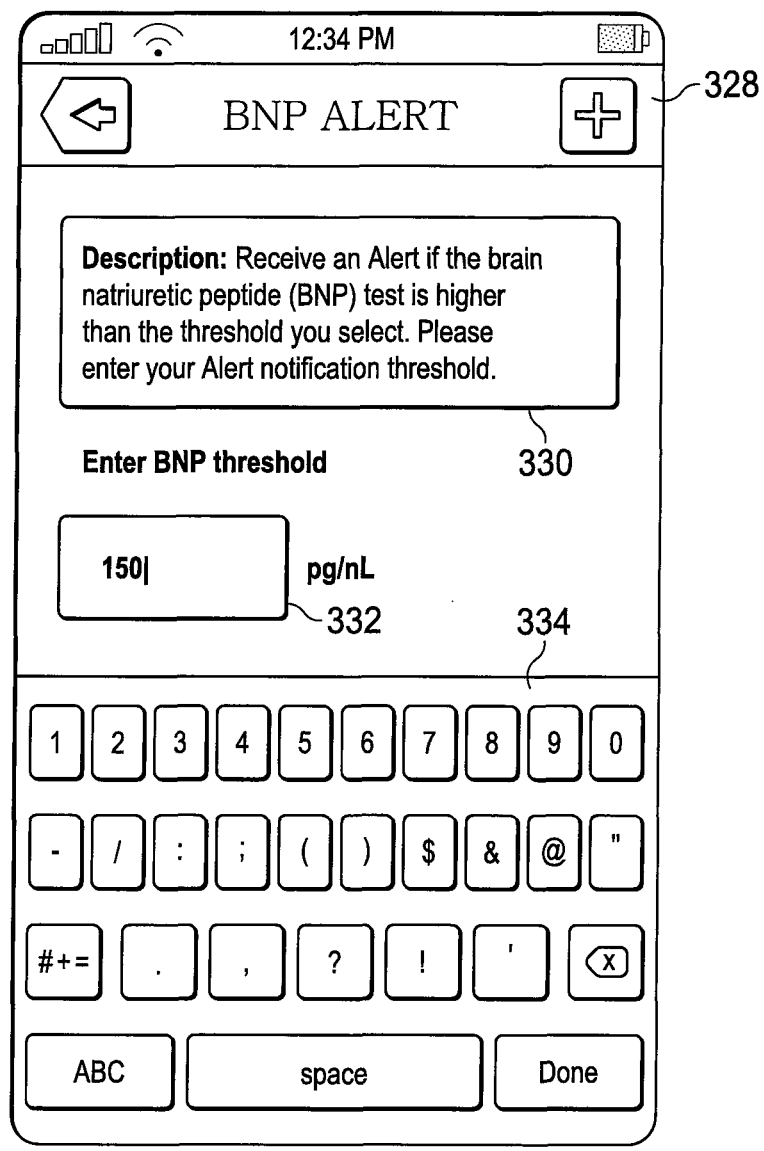
Figure 3H:
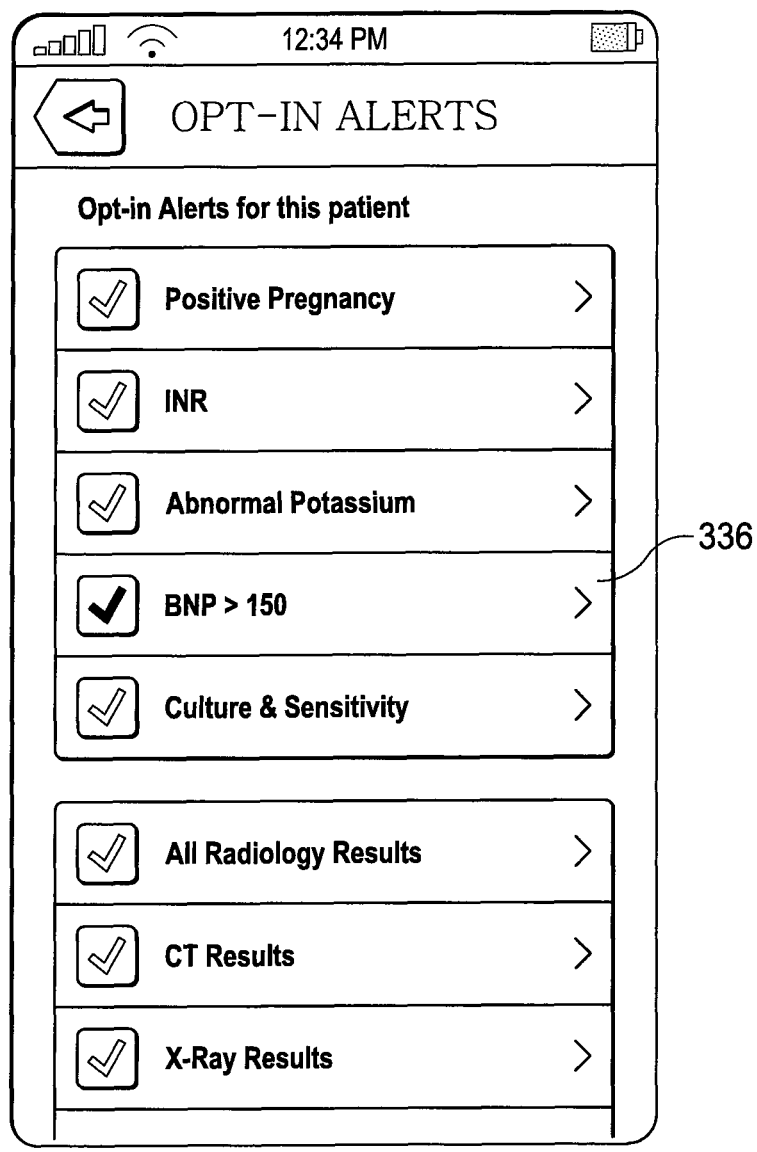

The user may select one or more of the displayed Alerts to "opt-in" on. In some embodiments, he can do so for all his patients or on a patient-by-patient basis. For example, the user may select "BNP test" 327 to go to a new page 328 for setting configuration of the new Alert (FIG. 3G). In the example illustrated, the page 328 includes a Description of the Alert 330, and one or more fields 332 and user interfaces 334 for entering configuration data. Once the Alert has been set, the screen would display a check mark next to the corresponding Alert identifier (FIG. 3H) 336.

Figure 3I:
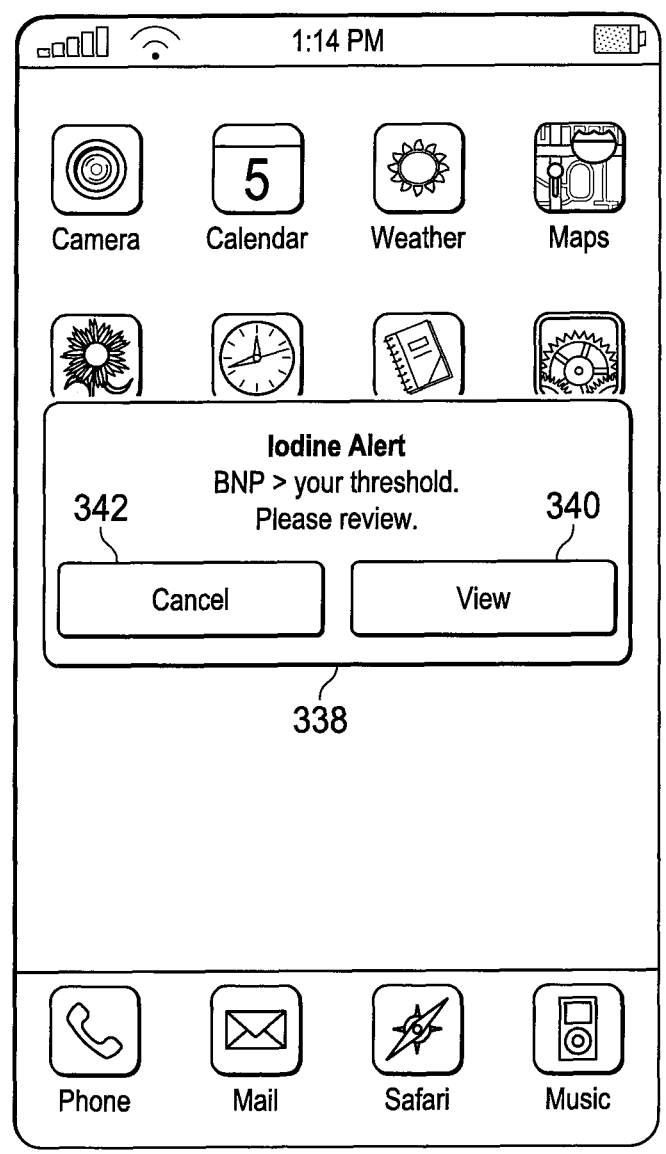
Figure 3J:
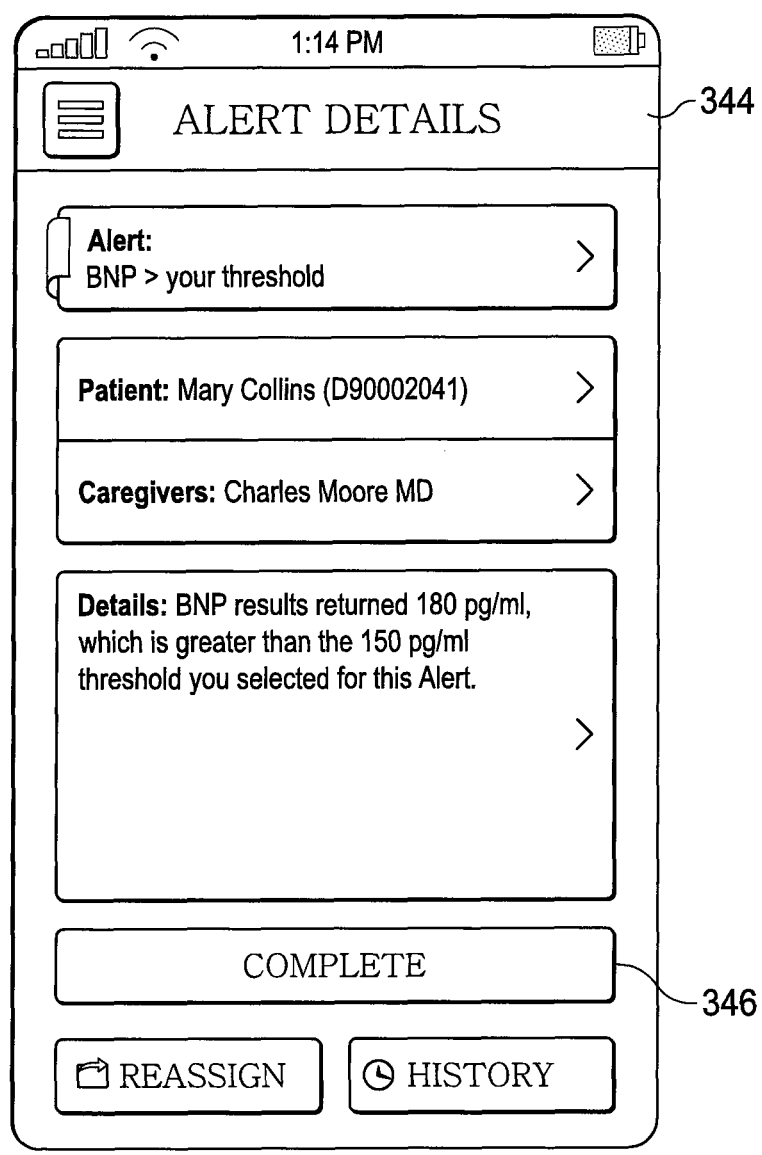
Figure 3K:
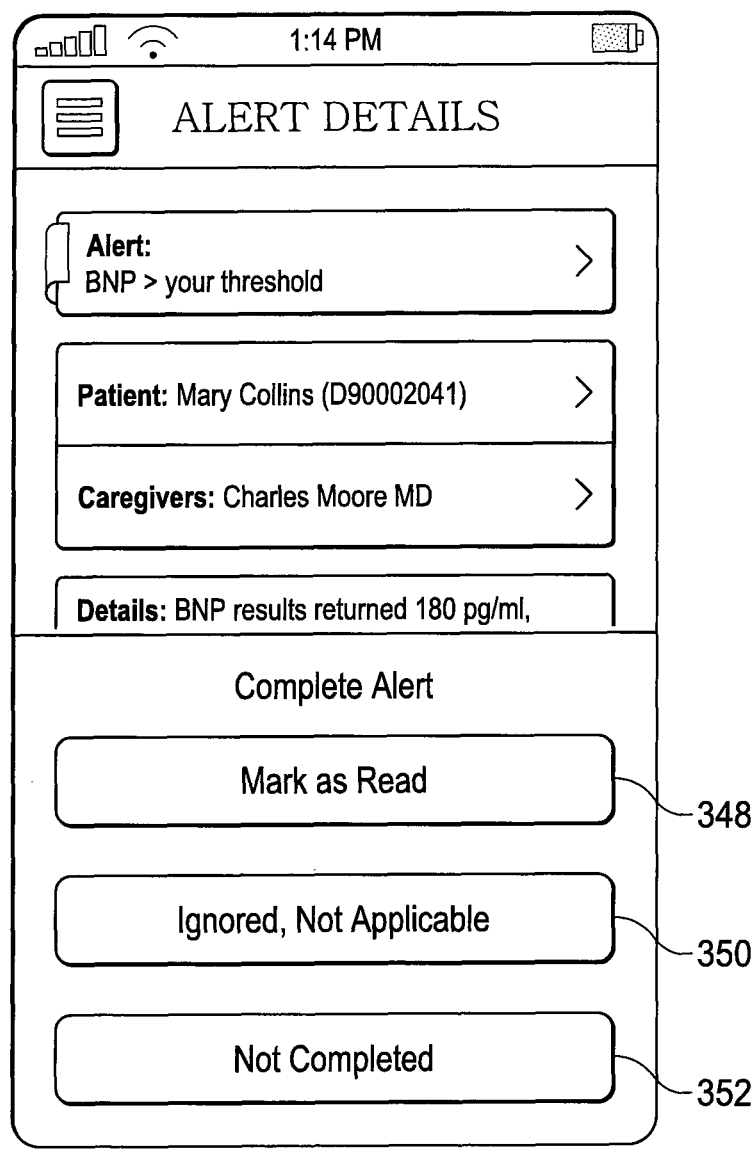
Figure 3L:
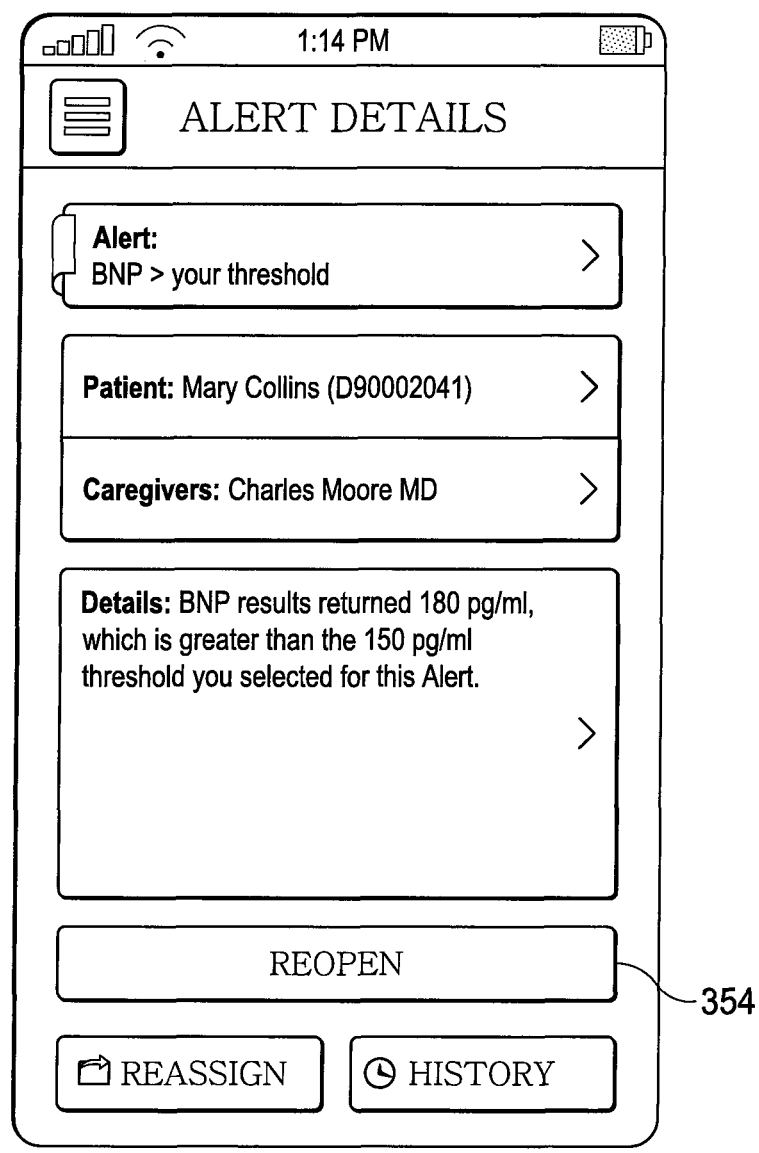

FIG. 3I illustrates an exemplary Alert 338 being received at the physician's user device. If he selects CANCEL 342, no further action will be taken. If he selects VIEW 340, he can get to the Alert Details screen 344 (FIG. 3J), which is similar to the Alert Details screen of FIG. 3C, but shows parameters particularized for the nature of the Alert (in this case, BNP). When an Alert has been viewed, the caregiver has options to complete the Alert by selecting the Complete button 346. As shown in FIG. 3K, these may include Mark as Read 348; Ignored, Not Applicable 350; or Not Completed 352. In some embodiments, a user may reopen an Alert once viewed using control button 354 (FIG. 3L).

Figure 3M:
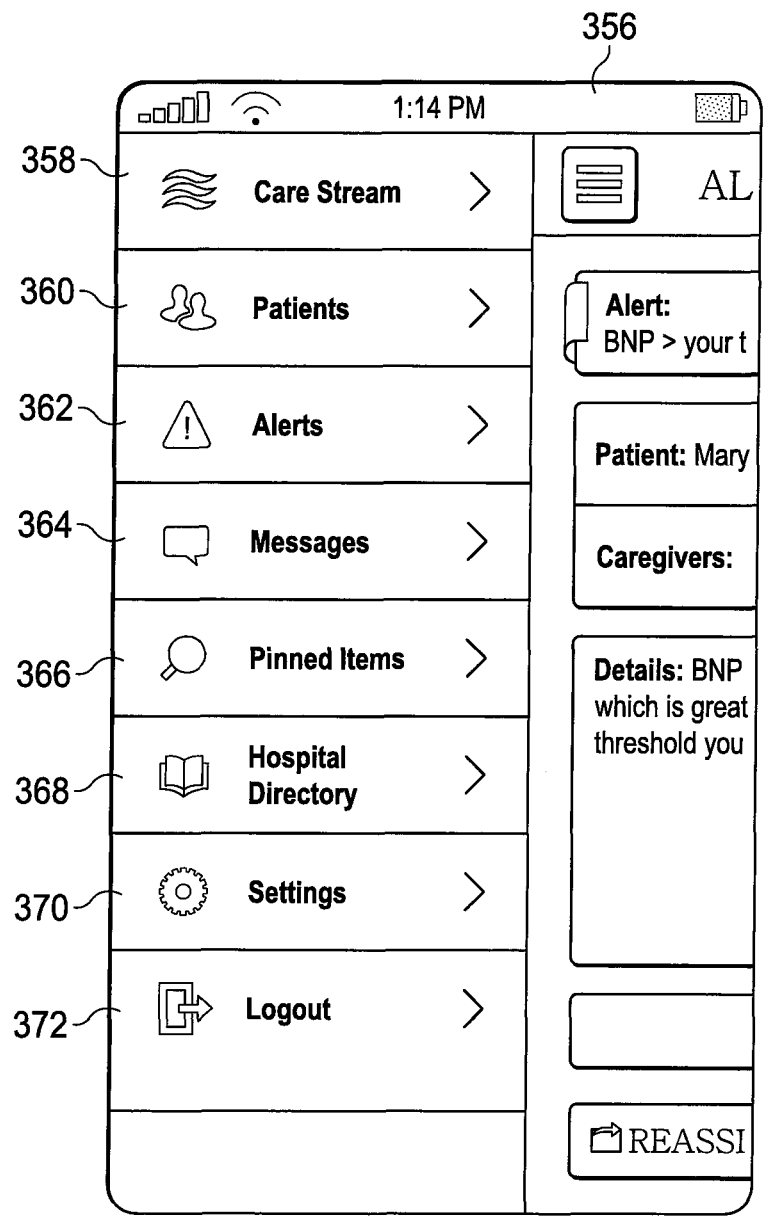

In some embodiments, a Main Menu 356 may be displayed (FIG. 3M), for example, by sliding from the left. The Main Menu 356 may include controls for viewing or interacting with items such as CareStream 358; Patients 360; Alerts 362; Messages 364; Pinned Items 366; Hospital Directory 368; Settings 370; Logout 372. Selecting main menu items may cause navigation to a new page.

Figure 3N:
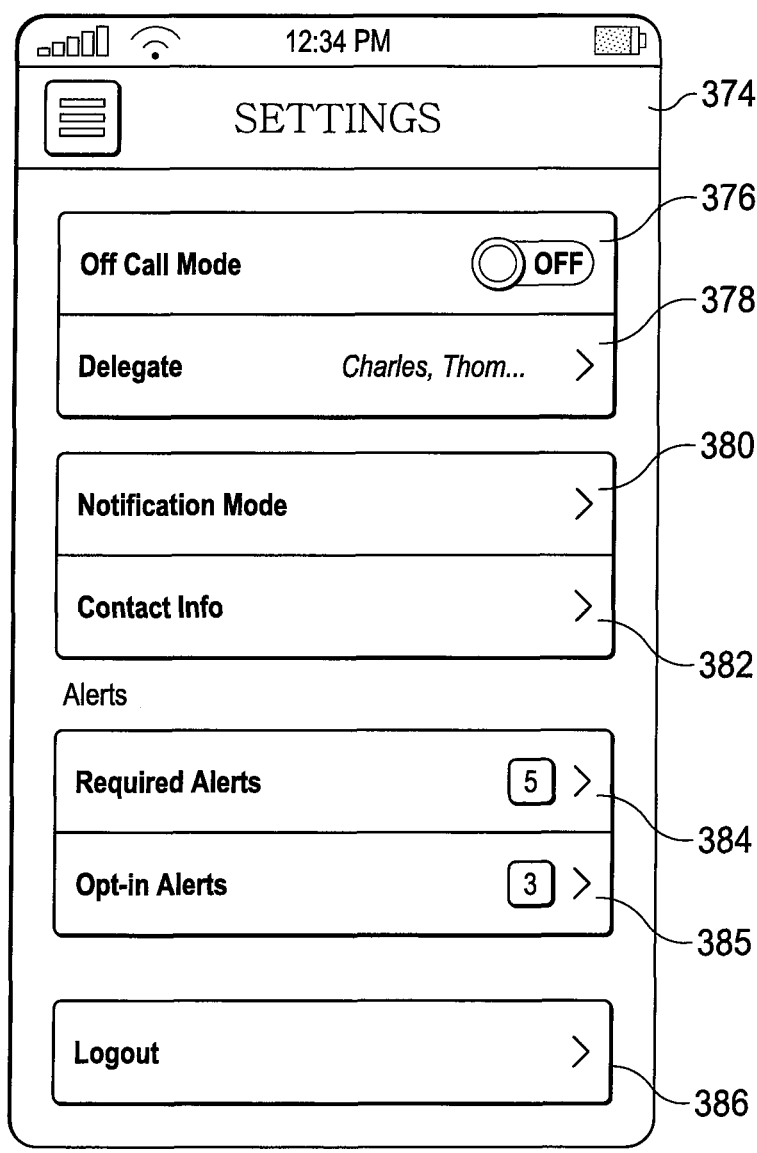

For example, if Settings 370 is selected, the user is navigated to a Settings page 374 (FIG. 3N). In the example illustrated, the Settings page includes Off Call Mode 376 and Delegate 378 settings; Notification Mode 380 and Contact Information 382 settings; Required Alerts 384 and Opt-In Alerts 385 settings; and Logout control 386.

Figure 3O:
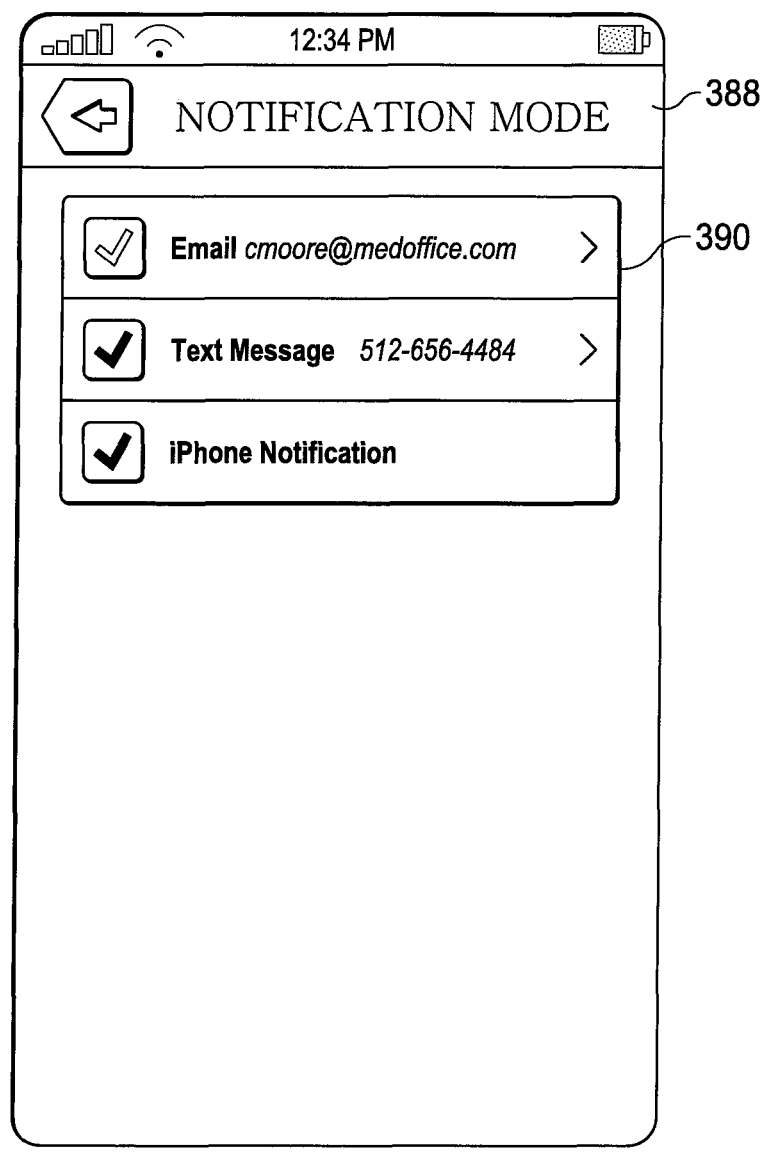

For example, if the caregiver selects Notification Mode 380, he can be navigated to a mode select page 388 (FIG. 3O), which allows him to select the media 390 by which a Notification is to be received. In the example illustrated, he may receive a Notification via email, text message, or telephone.

Figure 3P:
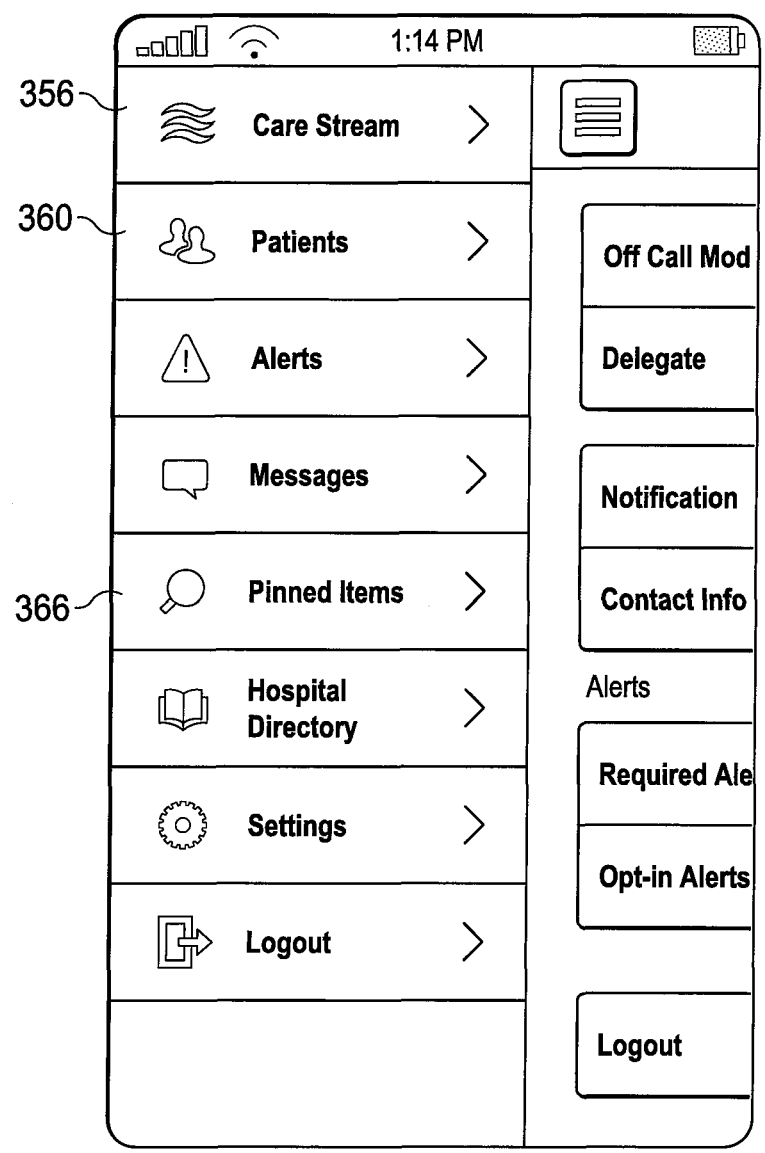
Figure 3Q:
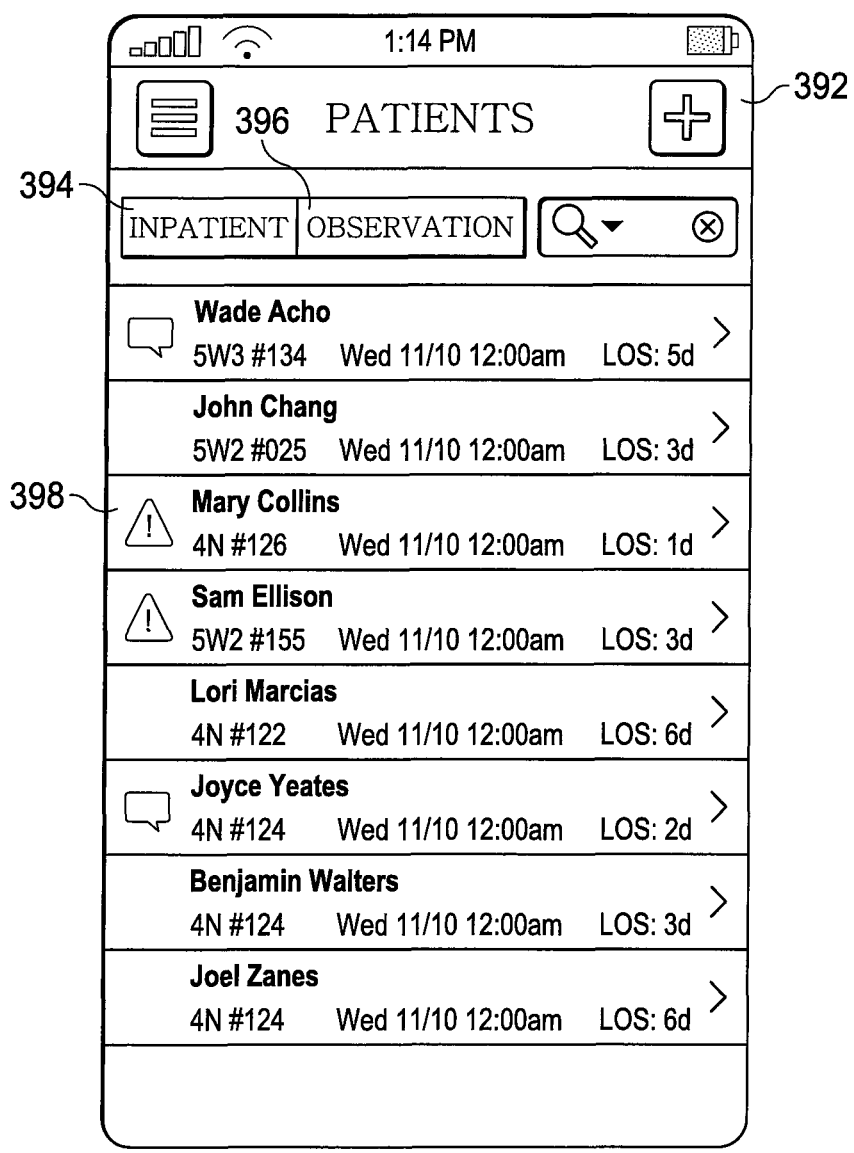

The caregiver may return to the Main Menu 356 (FIG. 3P) and select another Main Menu item, such as Patients 360. This displays a list of patients in the Patients screen 392 (FIG. 3Q). There can be tab selections to switch between Inpatient 394 and Observation patients 396. An area may be provided, e.g., to the left of patient name where icons 398 can be placed for each patient to indicate presence of an Alert or Message. For example, patient Mary Collins has an Alert icon displayed next to her name.

Figure 3R:
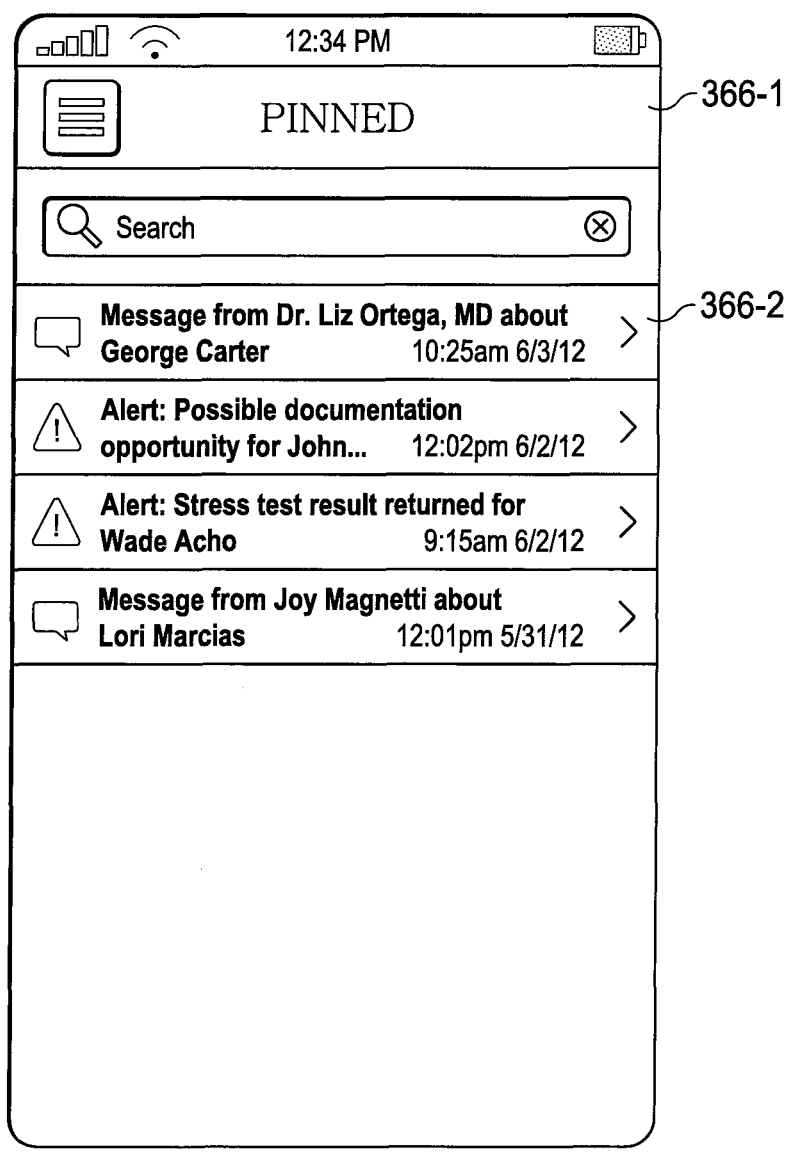
Figure 3S:
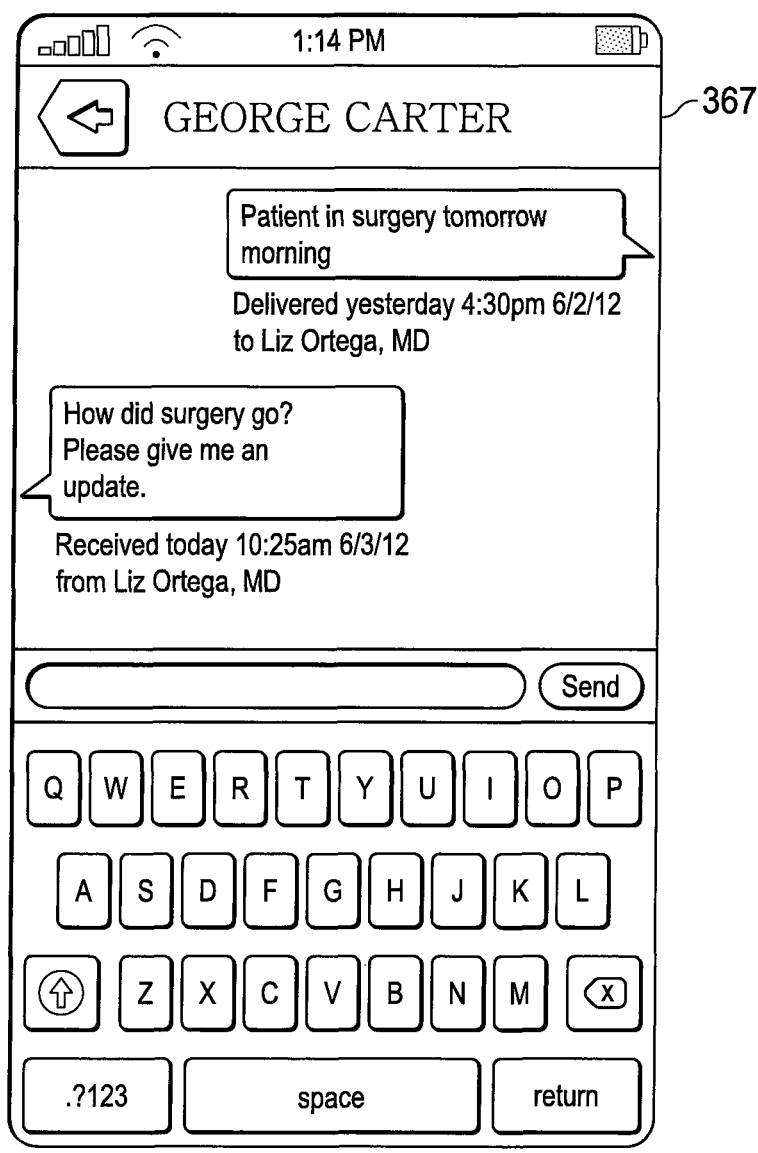

If, in the Main Menu 356, the user tapped on Pinned 366, a list of Pinned Items is displayed 366-1 (FIG. 3R), which can include messages and Alerts, for example. The User can tap on one of the pinned items, for example, "Message from Dr. Liz Ortega . . . " 366-2 to display the message screen 367 (FIG. 3S) and can allow a response.

Figure 3T:
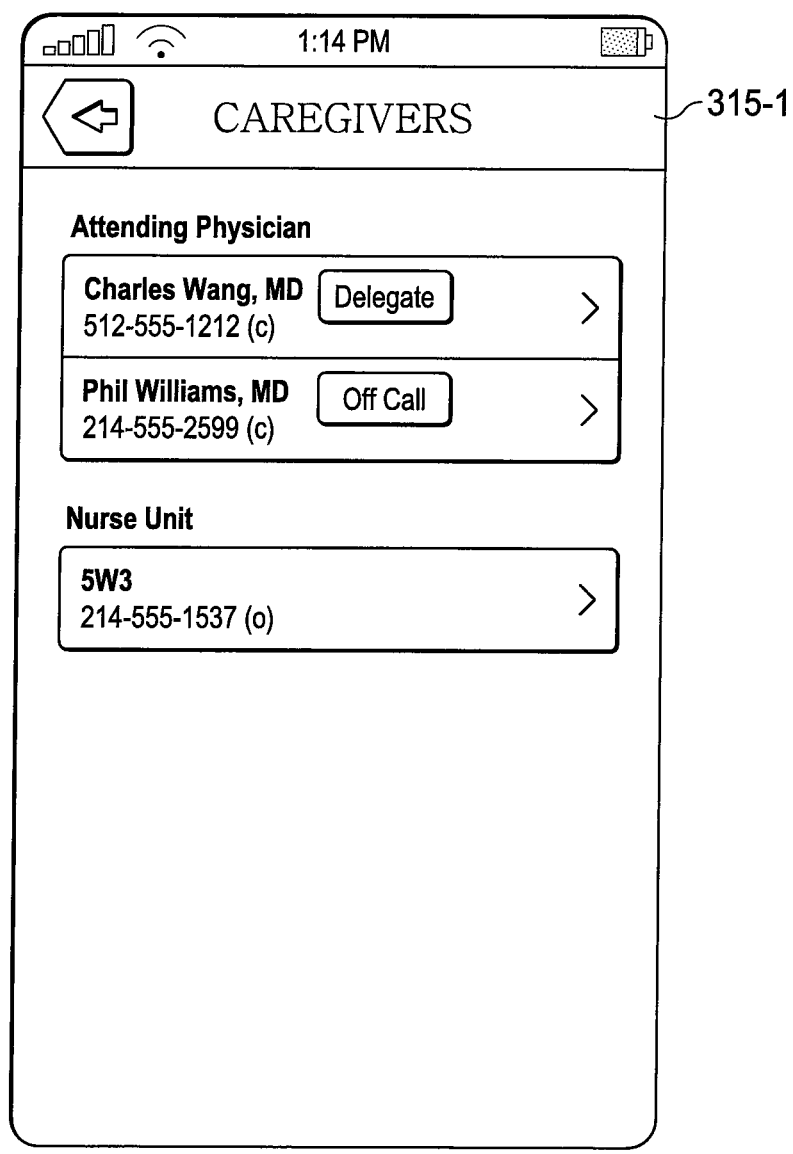
Figure 3U:
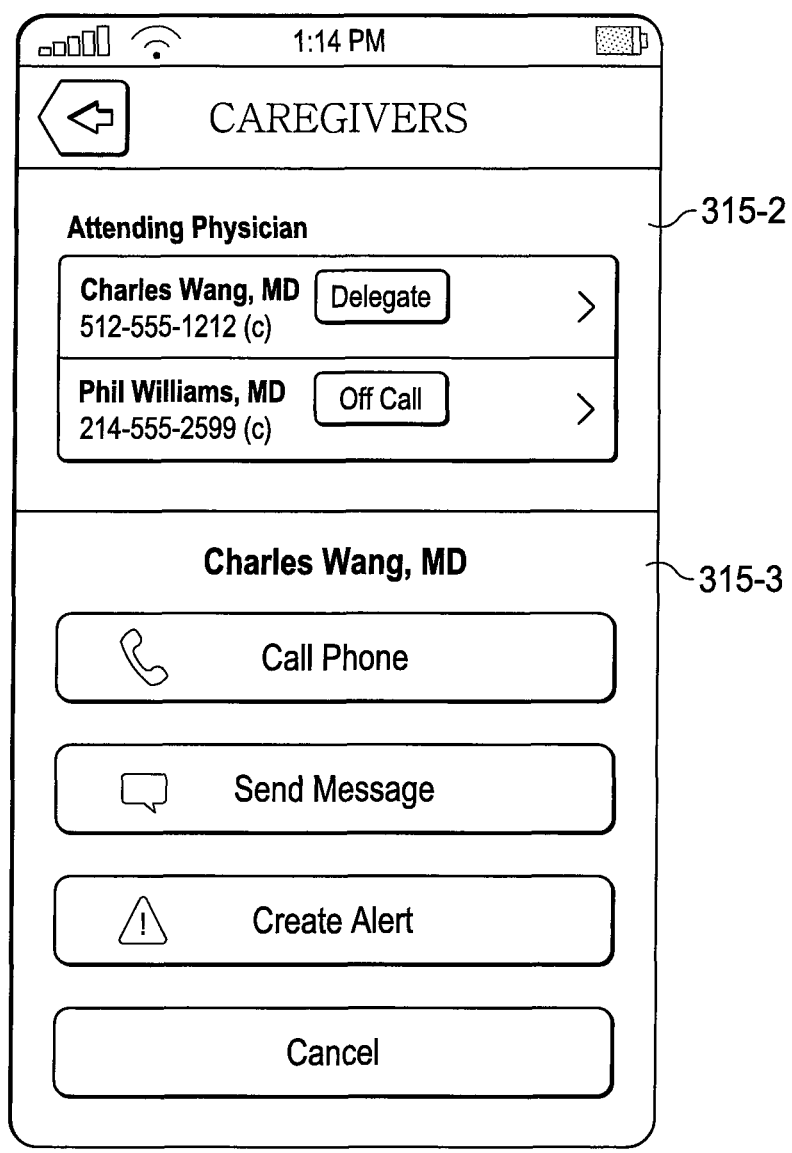

As shown in FIG. 3T and FIG. 3U, lists of caregivers 315-1, 315-2 associated with particular patients may be saved, as well as contact information 315-3. Such lists may be accessed, for example, by selecting a Caregivers link 316 (FIG. 3C).

Figure 3V:
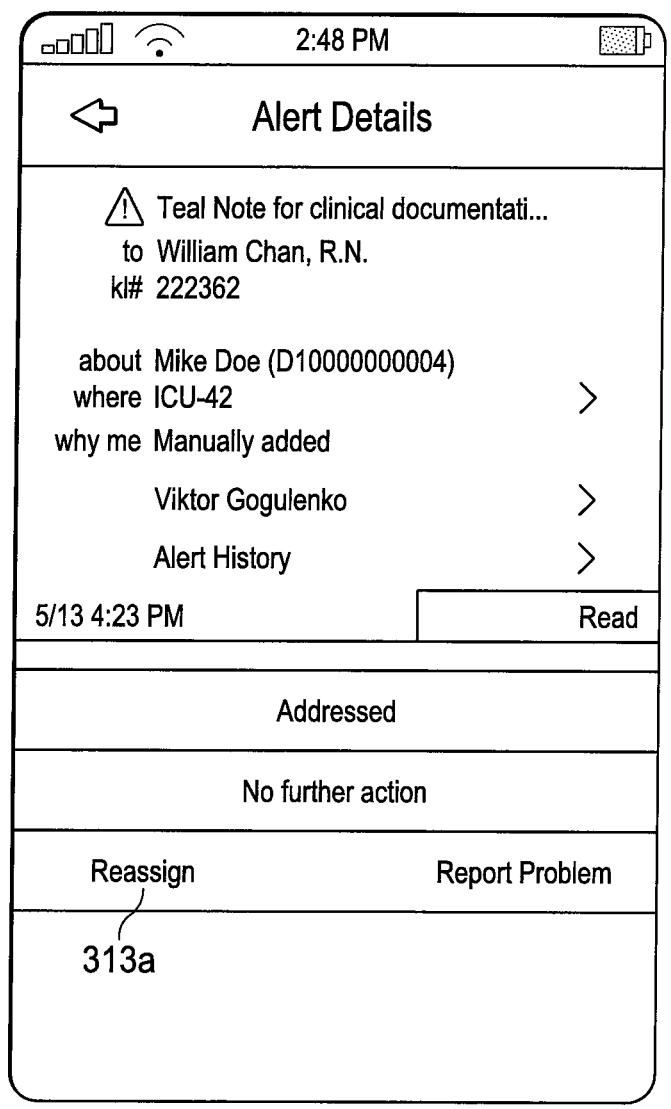
Figure 3W:
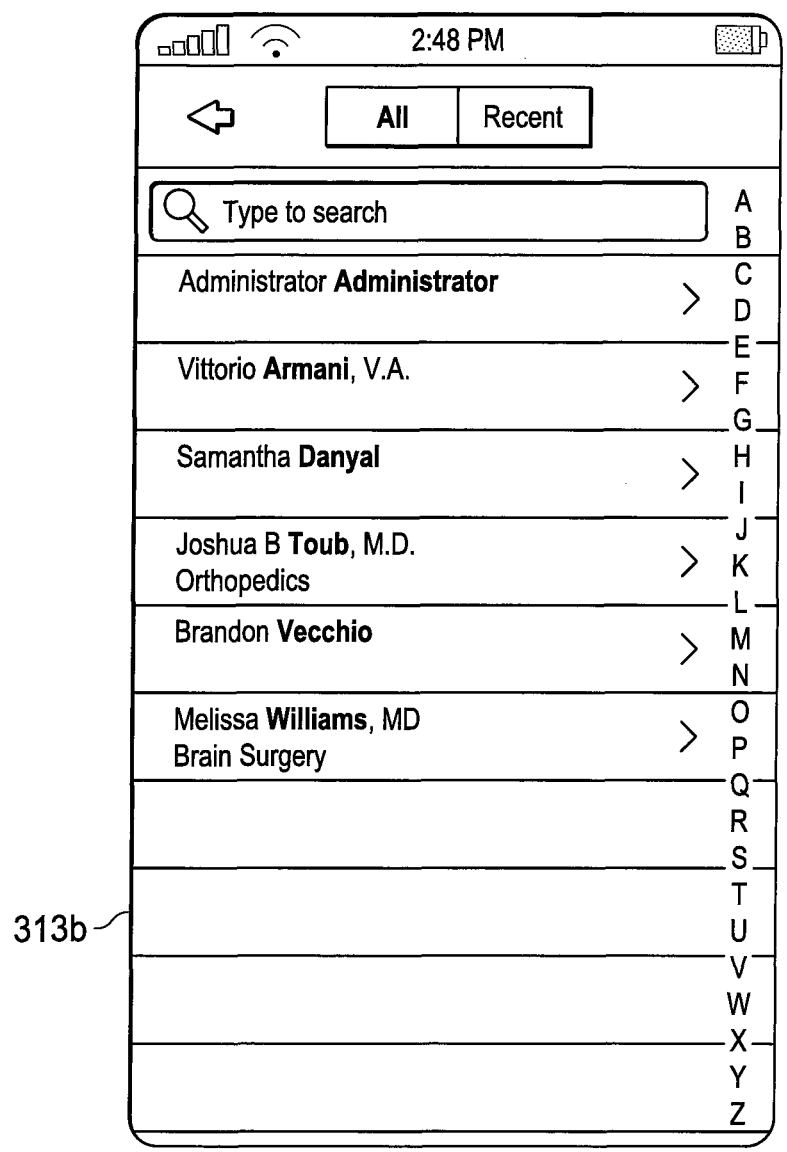
Figure 3X:
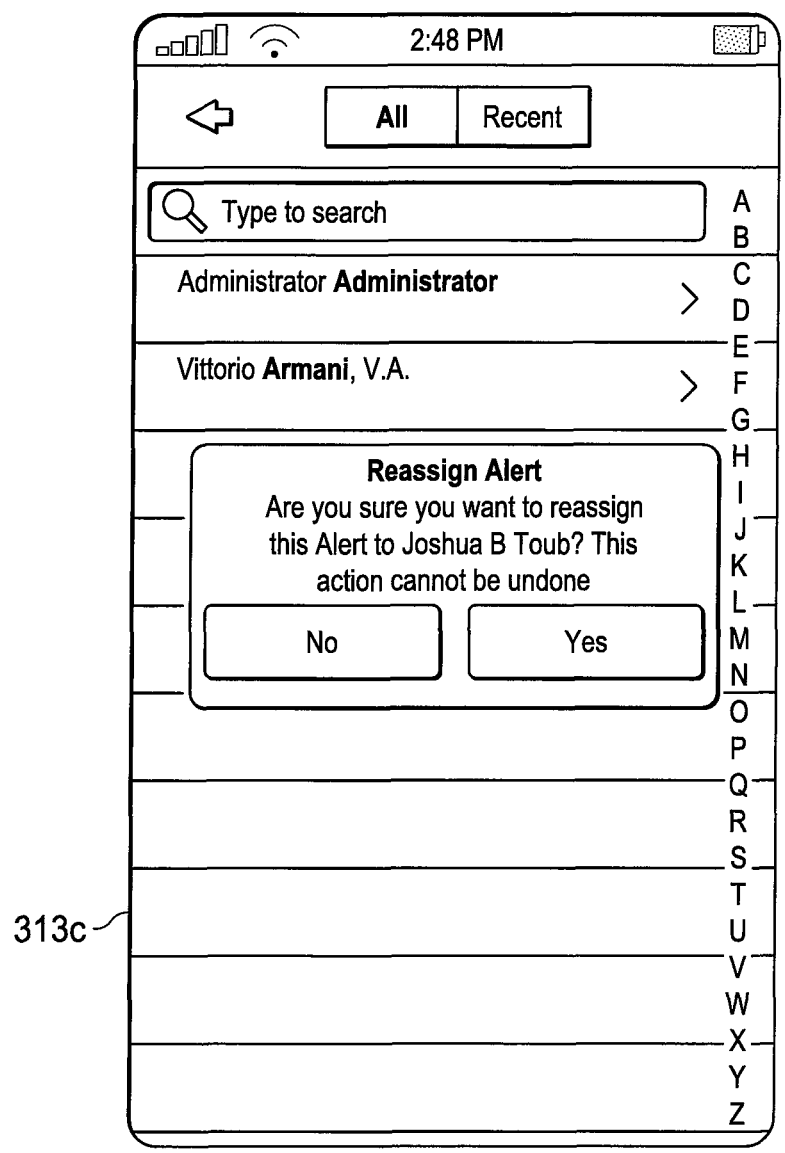

As noted above, a user may reassign an Alert if desired. For example, as shown in FIG. 3V, a user may select Reassign 313a and will be presented with list 313b (FIG. 3W) of names of users that may be selected to whom the Alert may be reassigned. The user may select the corresponding name to be presented with, for example, screen 313c (FIG. 3X) for confirmation that the user does indeed wish for the Alert to be reassigned. Once reassigned, in some embodiments, the Alert is removed from the user's list and moved to the selected recipient's list.

Figure 4:
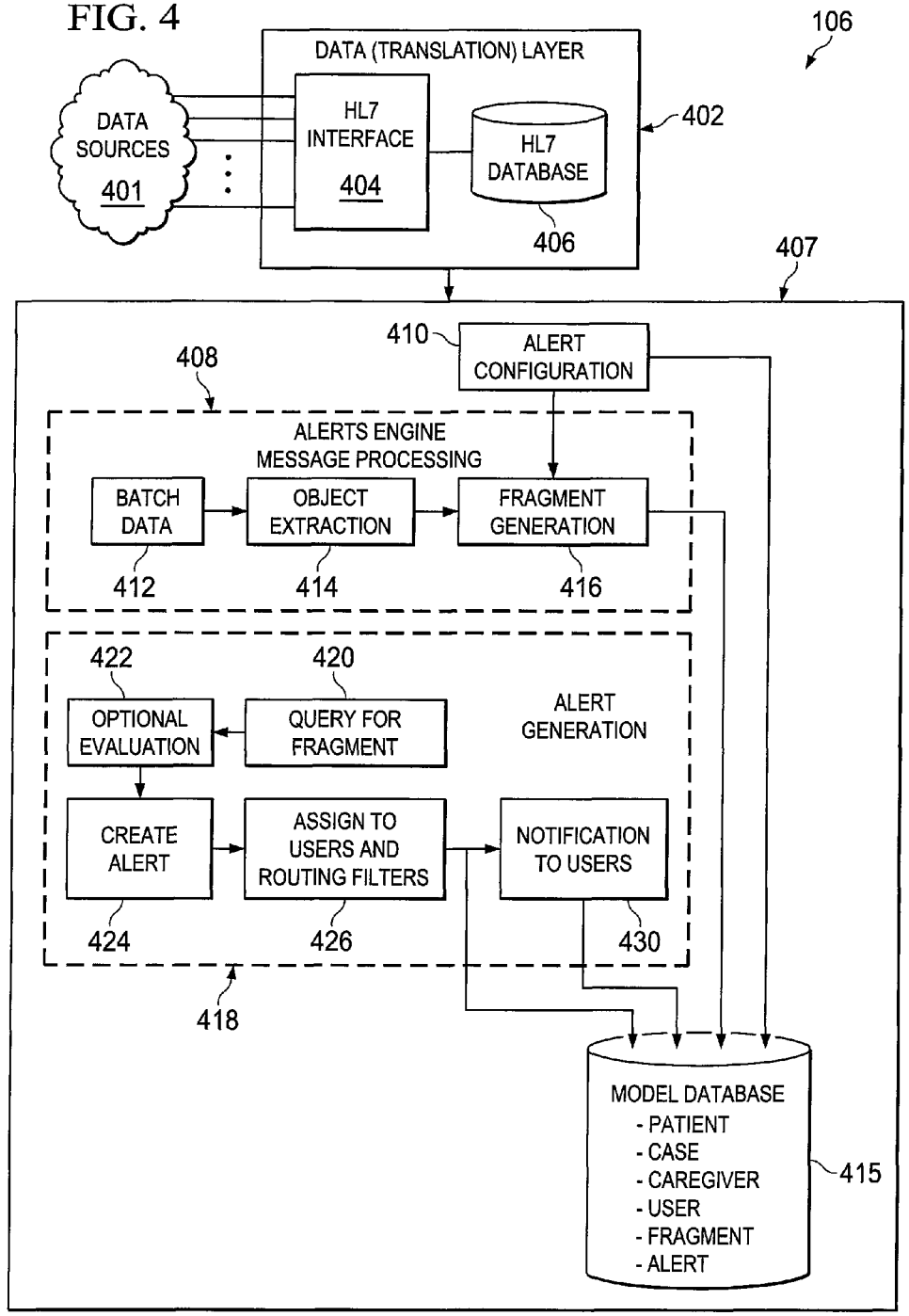
FIG. 4 illustrates an exemplary system for embodiments disclosed herein.

Turning now to FIG. 4, an exemplary RTMC system 106 is shown in greater detail. As illustrated, the RTMC 106 includes a data translation layer 402 including an interface engine 404 and database 406. In one embodiment, the interface engine 404 is an HL7 interface engine and the database 406 is an HL7 database. The interface engine 404 receives feeds 401 from the various hospital or care facility data sources 104, which typically are formatted as text messages, and maps them into rows and columns for the database 406. The database 406 stores the information in a relatively easy to use format. As noted above, the hospital feeds are typically maintained and updated in real time.

An exemplary HL7 message is shown below. In particular, shown below is a sample HL7 message representing the results of a CBC (complete blood count) lab procedure:
MSH|^~\& |LAB|IODINE |||201306121531||ORU^R01|ID12345|P|2.3|||||
PID|1||MRN12345|ACCT98765|1221|SMITH^BOB||1985 0608|M||12345 MAIN ST^AUSTIN^TX^^78701||||||ACCT98765|123-45-6789 ||||||||
PV1 |1|I|FACILITY.1|||||DRID12345^JOHNSON^SALLY||N ONE^None |||||||N||REF||IN||||||||||||||||||CMC||FACIL-ITY .1 |||201306101110|||||||
ORC |||||||||||||||||||
OBR|1|ORDER123^LAB|ORDER123^LAB^ALTORDER5 678|CBC^LABCBC|||201306111212 |||||||201 306111244||DRID12345^JOHNSON^SALLY||||||||LAB |F||^^^^^R|||||||

OBX|1|ST|WBC^WBC^L|8.7|K/uL|3.6-10.8|N||F|||201306111244||
OBX|2|ST|RBC^LAB RBC^L|1|4.83|M/uL|4.2-5.4|N||A^S|F|||201306111244||
OBX|3|ST|HGB^Hemoglobin^L|1|13.6|G/dL|12.0-16.0|N||A^S|F|||201306111244||
OBX|4|ST|HCT^Hematocrit^L|1|40.7|%|37-47|N||A^S|F|||201306111244||
OBX|5|ST|PLT^Platelet Count^L|1|390|K/uL|150-400|N||A^S|F|||201306111244||
OBX|6|ST|ST|MPV^MPV^L|1|10.2|fL|7.4-10.4|N||A^S|||201306111244||
OBX|7|ST|GRP^Gran % (Auto)^L|1|74.7|%|42-72|H|A^S|F|||201306111244||
OBX|8|ST|LYP^Lymph % (Auto)^L|1|18.9|%|20.5-51.1|L||A^S|F|||201306111244||
OBX|9|ST|MIDP^Mid Range % (Auto) ^L|1|6.4|%||N||A^S|F|||201306111244||
OBX|10|ST|GRA^Gran # (Auto)^L|1|6.5|K/uL|1.8-7.7|N||A^S|F|||201306111244||
OBX|11|ST|LYA^Lymph # (Auto)^L|1|1.6|K/uL|1.0-4.8|N||A^S|F|||201306111244||
OBX|12|ST|MIDA^Mid Range # (Auto)^L|1|0.6|K/uL-||N||A^S|F|||201306111244

The first line—the MSH "segment"—indicates that this is a result (indicated by the "ORU-R01"). The 2nd line—the PID segment—provides identifying information about the patient. In this case, the patient's name is Bob Smith; he lives at 12345 Main St., his medical record number is MRN12345, and his account number is ACCT98765.

The 3rd line—the PV1 segment—provides status information about the patient's current visit. In this case, it is simply indicating that he is an inpatient that was admitted on Jun. 10, 2013 at 11:10 am.

The 4th line—the OBR segment—provides information about the order that was previously placed that caused this lab procedure to be performed. In this case, it can be seen that Dr. Sally Johnson ordered the procedure with id "CBC" and named "LAB CBC" at 12:12 pm on Jun. 11, 2013.

The remaining lines each contain a single result. For example:
OBX|1|ST|WBC^WBC^L|8.7|K/uL|3.6-10.8|N||F|||2013061101244||
OBX=indicates that this line contains a result
1=indicates that this is the first result line returned for the order
ST=indicates that the result contains a simple string value.
WBC^WBC LAB^L=indicates that the result is a "WBC LAB" result with an ID of "WBC".
8.7=This is the actual numerical result
K/uL=These are the units of measure for the result
3.6-10.8=This is the reference range for this particular result
N=This is where abnormality flags would be. N indicates "normal".
F=Final status
201306111244=Observation occurred at 12:44 pm on Jun. 11, 2013

Upon processing by the HL7 interface engine 404, this message would create a plurality of rows in a LabResult table (not shown) of the hospital data HL7 database 406.

The database information is used by an Alerts engine 407 to define and generate Alerts and Notifications. More particularly, in an Alerts Engine Message Processing module 408, a source definition module 412 batch processes predetermined amounts of data from each of the hospital feed sources (i.e., by type of feed, such as ADT, Orders, etc.) one source at a time. In particular, in some embodiments, each type of data is associated with a table and the tables are processed one at a time, as discussed above.

The batch data is then passed to an entity extraction module 414, which identifies whether there is a business object of interest or a modification to an existing business object. A new business object, also referred to as an entity, may be a new patient, case, caregiver, test result, procedure order, etc. For example, if there is a new patient, or doctor, or combination thereof, a new database entry will be constructed therefor.

Returning to the example given above, depending on the configuration, when the Alerts engine 407 processes these rows, it would extract (create) or update (if necessary) an entity for the physician referenced in the message, and could create one or more fragments from the various OBX lines. The entity created or updated in this case would be a "Caregiver". In this case, the system may:

Look up a Caregiver in the Model DB with ID "DRID12345".

Create a Caregiver for this ID if it doesn't exist.

Set the first name to "SALLY" and the last name to "JOHNSON".

Save the Caregiver to the Model DB 415.

In some embodiments, no other entities would be created from these rows in the HL7 DB 406 because patient-related information is not extracted from result messages. However, if this were an ADT (Admit/Discharge/Transfer) message, a number of different entities (Patient, Case, other Caregivers) may be created and/or updated.

As noted above, the results of the entity extraction are provided to a model database 415 and may be provided to a fragment generation module 416.

In some embodiments, the fragment generation module 416 also looks at the batch data to identify pieces of information that one or more of the Alerts might be interested in. That is, it looks for data which may be required for an Alert. Fragments are thus events of interest that are extracted from the batch data and used to make intelligent determinations of when an Alert should be generated. Fragments may be of different types. An Alert may be generated from one or more fragments. The fragment generation result is stored in one or more databases, such as model database 416.

For example, two fragment definitions may be defined as follows:

"wbcFD" configures an instance of the generic fragment definition "GenericNumericLabResultFD" to look for WBC results. Using the configured "observationIdsForMatch" parameter, this fragment looks at rows from the LabResult table in the HL7 database 406 whose orderServiceId field is "WBC". If a row of data from the HL7 database 406 matches the fragment definition, then a Fragment is created and a number of fields are set on the fragment. Much of the data set on the fragment is controlled by the semantics of GenericNumericLabResultFD. In this case, the system may automatically set the patient ID, case ID, ordering physician ID, observation ID, order ID, order name, observation value, observed results date, and message control ID. From the XML configuration for this fragment definition, the system may also set the units.

Looking back at the HL7 example above, this fragment definition would match the LabResult row created from the first OBX segment. This would create a Fragment with the following fields:

Fragment.patientId="MRN12345" (patient ID)
Fragment.caseId="ACCT98765" (case ID)
Fragment.str1="8 . . . 7" (observation value as a string)
Fragment.str2="K/uL" (units for observation)
Fragment.str3="CBC" (ID of ordered procedure)
Fragment.str4="LAB CBC" (name of ordered procedure)
Fragment.str5="ORDER123" (order number)
Fragment.str6="N" (abnormality flag)
Fragment.str7="1" (first result)
Fragment.cgId1="DRID12345" (ID of ordering physician)
Fragment.fp1=8.7 (numerical value for observation)
Fragment.date1=6/11/2013 12:12 pm (order time/date)
Fragment.date2=6/11/2013 12:44 pm (observation time/date)

This Fragment would then exist in the Model database 415 and be available for Alert Rules to process.

Similarly, the second fragment definition would match any result rows with an observation ID of either "HG B" or "ZZHGB". In this case, it would create a Fragment populated with the data contained in the third row created from the HL7 message above.

In general, any number (e.g., hundreds) of fragments of different types may be defined. For example:

wbcFD—captures white blood cell count
hgbFD—captures hemoglobin values
ctResultFD—captures the results of a Cat Scan report

```
<bean id="wbcFD"
class="com.iodinesoftware.rta.alertsengine.rules.fragment.GenericNumericLabResultFD">
<property name="observationIdsForMatch" value="WBC" />
<property name="msgFieldMap">
        <map>
            <entry key="units" value="str2" />
        </map>
    </property>
    </bean>
<bean id="hgbFD"
class="com.iodinesoftware.rta.alertsengine.rules.fragment.GenericNumericLabResultFD">
    <property name="observationIdsForMatch" value="HGB,ZZHGB" />
    <property name="deactivationPolicy"
ref="ageBasedFragmentDeactivationPolicy3" />
    <property name="lowerThreshold" value="12" />
    <property name="upperThreshold" value="16" />
    <property name="invert" value="true" />
    <property name="msgFieldMap">
        <map>
            <entry key="units" value="str2" />
        </map>
    </property>
</bean>
``` microFD—captures culture and sensitivity results from a culture transferFD—captures a patient transfer event bunCreatResultFD—captures the numerical value of either a BUN (Blood Urea Nitrogen) or Creatinine result directAdmitFD—captures that a direct admit event happened dischargePlanningConsutOrderedFD—captures that a discharge planning consult has been ordered Alert configuration module 410 defines rules for potential Alerts and fragments of Alerts. The Alert configuration rules may be dynamically configured by users, on an ongoing basis, as will be explained in greater detail below. Alternatively, or in addition, configuration rules may be set by a care facility, such as a hospital. The Alert configuration module 410 thus stores definitions of events that are of interest to a particular user. Each Alert has a fragment definition and a configuration rule.

The Alert Generation module 418 includes a query module 420 that queries the model database 416 for cases (a state of a visit) or fragments (for each Alert rule from 410) or combinations thereof. The evaluation module 422 performs one or more predetermined evaluations on the fragments to determine if particular criteria have been met. A query can query based on the case state (even if no other fragment occurs).

If the evaluations are successful, an Alert is generated 424. For each Alert, one or more routing filters 426 may be applied. That is, each Alert may be assigned to one or more of the users of user devices 108, 110. As noted above, the users are members or subscribers to the RTMC 106. It is noted that, in some instances, the Alerts may simply be stored or discarded and in others, may be maintained for presentation to a user and a Notification sent to the user at 440. The Notification can include log in information for the user to access the Alert.

In some embodiments, an Alert can be assigned to a single user or to a group of users. In some embodiments, more than one Alert may be created for the same set of data or may be "cloned" or copied for more than one user with independent workflows.

Configurable routing rules may apply for each Alert. In some embodiments, these can include filters and a target selection policy. A filter may include, for example, sending a Notification to a user at a particular time or if a particular value of medical data is exceeded for a particular patient, etc.

The target selection policy chooses the user to be assigned the Alert. This can include, for example, case manager, attending physician, admitting physician, or other specifically named user. In addition, other users may be able to elect to opt in to receiving a particular Alert. If the user(s) elected not to receive a Notification at a particular time, the Alert may be stored in the model database such that the next time the user logs in to the RTMC system 106, he will be shown the Alert. In some embodiments, the hospital or care facility may override the user's settings on an individual basis.

Configuration of fragments and Alerts is discussed below by way of example. In particular, in the example discussed, an Alert is to be generated for a particular patient if an unnecessary echocardiogram is performed (or to be performed). In such an example, three fragments are defined: Match Any Data from an Order Table of an Echocardiogram recently ordered; existence of a recent result of an echocardiogram; and only heart failure patients with an elevated BNP result.

```
<bean id="bnpResultFD"
class="com.iodinesoftware.rta.Alertsengine.rules.fragment.GenericLabResultFD">
        <property name="name" value="bnpResultFD" />
        <property name="observationIdsForMatch" value="BNP" />
        <property name="handleLargeResultStrings" value="false" />
        <property name="deactivationPolicy"
ref="ageBasedFragmentDeactivationPolicy5" />
    </bean>
<bean id="elevatedBnpFilter"
class="com.iodinesoftware.customers.cov.rta.Alertsengine.QueryFilter">
        <property name="query">
            <value><![CDATA[
                SELECT f FROM Fragment f WHERE f.fragmentDefName =
'bnpResultFD' AND f.fp1 >= 100 AND f.caseId = :caseId
            ]]></value>
        </property>
    </bean>
<bean id="echoOrderFD"
class="com.iodinesoftware.rta.Alertsengine.rules.fragment.GenericOrderFD">
        <property name="name" value="echoOrderFD" />
        <property name="orderServiceIdsForMatch" value="ECHO" />
        <property name="deactivationPolicy"
ref="ageBasedFragmentDeactivationPolicy4" />
    </bean>
    <bean id="echoResultFD"
class="com.iodinesoftware.rta.Alertsengine.rules.fragment.GenericLabResultFD">
        <property name="name" value="echoResultFD" />
        <property name="orderServiceIdsForMatch" value="ECHO" />
        <property name="handleLargeResultStrings" value="true" />
        <property name="deactivationPolicy"
ref="ageBasedFragmentDeactivationPolicy4" />
    </bean>
      <bean id="recentEchoAR"
class="com.iodinesoftware.rta.Alertsengine.rules.Alert.GenericQueryAR">
        <property name="name" value="recentEchoAR" />
        <property name="admissionStatusFilter"
value="INPATIENT,OBSERVATION" />
        <property name="frequency" value="NO_LIMIT" />
        <property name="query">
```

```
            <value><![CDATA[
                    SELECT f1, f2 FROM Fragment f1, Fragment f2
                        WHERE
                            f1.active = true
                            AND f1.fragmentDefName = 'echoOrderFD'
                            AND f2.fragmentDefName = 'echoResultFD'
                            AND f2.str7 = '1'
                            AND f1.patientId = f2.patientId
                            AND f1.date1 > f2.date2
                            AND timestampdiff(DAY, f2.date2,
f1.date1) <= 182
            ]]></value>
        </property>
        <property name="additionalFragmentsQuery">
            <value><![CDATA[
                    SELECT f FROM Fragment f
                        WHERE
                            f.fragmentDefName = 'echoResultFD' AND
f.patientId = :patientId
                            AND f.date2 = (SELECT max(f2.date2) FROM
Fragment f2 WHERE f2.fragmentDefName = 'echoResultFD' AND f2.patientId =
:patientId)
                        ORDER BY f.long5
            ]]></value>
        </property>
```

Once the fragments are defined, one or more filters may be provided. Such filters may define, for example, an age of patient or other parameters associated therewith.

```
<property name="filters">
    <list>
        <bean
class="com.iodinesoftware.rta.Alertsengine.impl.PatientAgeAlertFilter" >
            <property name="minAge" value="18" />
        </bean>
        <bean
class="com.iodinesoftware.rta.Alertsengine.impl.CaseAttrAlertFilter" >
            <property name="attrMatches">
                <map>
                    <entry key="facility" value="*,!CPH"
/>
                </map>
            </property>
        </bean>
        <bean
class="com.iodinesoftware.rta.Alertsengine.impl.CompositeAlertFilter" >
            <property name="filterExpression"
value="elevatedBnpFilter|historyOfChfFilter" />
        </bean>
    </list>
</property>
<property name="signatureFields" value="str1" /> <!-- order # for
current order -->
<property name="routingRules">
    <list>
        <!-- Default rule -->
        <bean
class="com.iodinesoftware.rta.Alertsengine.rules.Alert.BaseAlertRoutingRule">
            <property name="selectionPolicy">
                <bean
class="com.iodinesoftware.rta.policies.impl.NamedUserAlertTargetSelectionPolicy"
>
                    <property name="username"
value="sysadmin" /> <!-- TODO: Update to real recipient! -->
                </bean>
            </property>
        </bean>
    </list>
</property>
```

The Alert itself may then be generated from the fragments and filters:

```
<property name="title" value="Echocardiogram within the past 6 months" />
    <property name="shortDescription" value="Echo within past 6 months" />
    <property name="fullDescription">
        <value><![CDATA[
            <div class="Alert-desc-title">
                Echocardiogram within the past 6 months
            </div>
            <div class="Alert-desc-desc">
                Receive a Notification when an Echocardiogram has been ordered, the patient had one within the past 6 months, and the patient either has a history of CHF and/or has a BNP result > 100.
            </div>
            <div class="Alert-desc-recpt">
                Recipient: TBD
            </div>
        ]]></value>
    </property>
```

Finally, a message template may be used to send a Notification if the criteria of the fragments and filters are fulfilled. In the example illustrated, text indicating that an echocardiogram has been performed in the last six months, results of a current order, and previous results.

```
<property name="messageTemplate">
    <value><![CDATA[
        #set($diagnosisStr = $covFormatUtils.icd9DiagnosisAlertFormat($case.initialIcd9Diagnosis))
        #set($cg1 = ${cgSvc.findByHospitalId($frag1.cgId1)} )
        #set($cg4 = ${cgSvc.findByHospitalId($frag4.cgId1)} )
        This patient has an Echocardiogram ordered and had one within the past 6 months. <br/>
        <div id="Alert-msg-details" style="padding:8px;">
            <table>
                <tr><td style="padding-right:4px;">Patient name:</td><td>${formatUtils.nameFormat($case.patient)}</td></tr>
                <tr><td style="padding-right:4px;">Location:</td><td>$!{formatUtils.formatLocation($case.locationPointOfCare,$case.locationRoom,$case.locationBed)}</td></tr>
                #if($diagnosisStr && !$diagnosisStr.equals("N/A"))
                <tr><td style="padding-right:4px;">Admitting diagnosis:</td><td>$!{formatUtils.icd9DiagnosisAlertFormat($case.initialIcd9Diagnosis)}</td></tr>
                #else
                <tr><td style="padding-right:4px;">Chief complaint:</td><td>$!{case.chiefComplaint}</td></tr>
                #end
            </table>
            Current echocardiogram order details:
            <table>
                <tr><td style="padding-right:4px;">Ordered by:</td><td>#if(!$cg1)<i>Unknown</i>#else${formatUtils.nameFormatWithSpecialty($cg1)}#end</td></tr>
                <tr><td style="padding-right:4px;">Order #:</td><td>$!{frag1.str1}</td></tr>
                <tr><td style="padding-right:4px;">Procedure ordered:</td><td>$!{frag1.str2} $!{frag1.str4}</td></tr>
            </table>
            Previous echocardiogram result details:
            <table>
                <tr><td style="padding-right:4px;">Account #:</td><td>$!{frag4.caseId}</td></tr>
                <tr><td style="padding-right:4px;">Ordered by:</td><td>#if(!$cg4)<i>Unknown</i>#else${formatUtils.nameFormatWithSpecialty($cg4)}#end</td></tr>
                <tr><td style="padding-right:4px;">Order #:</td><td>$!{frag4.str5}</td></tr>
                <tr><td style="padding-right:4px;">Procedure ordered:</td><td>$!{frag4.cgId2} $!{frag4.cgId4}</td></tr>
                <tr><td style="padding-right:4px;">Observation date:</td><td>$!{formatUtils.shortDateFormat($frag4.date2)}</td></tr>
            </table>
        </div>
        #if($fragments.size() > 4)
        <div class="lab-comments"><code style="white-space: pre;">#foreach($frag in $fragments)#if($velocityCount > 4)$!{formatUtils.formatTextBlob($frag.txt1)}<br/>#end#end</code></div>
        #end
    ]]></value>
</property>
```

```
    <property name="criticality" value="CRITICAL" />
    <property name="optional" value="true" />
</bean>
```

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

Any suitable programming language can be used to implement the routines, methods or programs of embodiments of the invention described herein, including C, C++, Java, assembly language, etc. Different programming techniques can be employed such as procedural or object oriented. Any particular routine can execute on a single computer processing device or multiple computer processing devices, a single computer processor or multiple computer processors. Data may be stored in a single storage medium or distributed through multiple storage mediums, and may reside in a single database or multiple databases (or other data storage techniques). Although the steps, operations, or computations may be presented in a specific order, this order may be changed in different embodiments. In some embodiments, to the extent multiple steps are shown as sequential in this specification, some combination of such steps in alternative embodiments may be performed at the same time. The sequence of operations described herein can be interrupted, suspended, or otherwise controlled by another process, such as an operating system, kernel, etc. The routines can operate in an operating system environment or as stand-alone routines. Functions, routines, methods, steps and operations described herein can be performed in hardware, software, firmware or any combination thereof.

Embodiments described herein can be implemented in the form of control logic in software or hardware or a combination of both. The control logic may be stored in an information storage medium, such as a computer-readable medium, as a plurality of instructions adapted to direct an information processing device to perform a set of steps disclosed in the various embodiments. Based on the disclosure and teachings provided herein, a person of ordinary skill in the art will appreciate other ways and/or methods to implement the invention.

It is also within the spirit and scope of the invention to implement in software programming or code any of the steps, operations, methods, routines or portions thereof described herein, where such software programming or code can be stored in a computer-readable medium and can be operated on by a processor to permit a computer to perform any of the steps, operations, methods, routines or portions thereof described herein. The invention may be implemented by using software programming or code in one or more general purpose digital computers, by using application specific integrated circuits, programmable logic devices, field programmable gate arrays, and so on. Optical, chemical, biological, quantum or nanoengineered systems, components and mechanisms may be used. In general, the functions of the invention can be achieved by any means as is known in the art. For example, distributed, or networked systems, components and circuits can be used. In another example, communication or transfer (or otherwise moving from one place to another) of data may be wired, wireless, or by any other means.

A "computer-readable medium" may be any medium that can contain, store, communicate, propagate, or transport the program for use by or in connection with the instruction execution system, apparatus, system or device. The computer readable medium can be, by way of example only but not by limitation, an electronic, magnetic, optical, electromagnetic, infrared, or semiconductor system, apparatus, system, device, propagation medium, or computer memory. Such computer-readable medium shall generally be machine readable and include software programming or code that can be human readable (e.g., source code) or machine readable (e.g., object code). Examples of non-transitory computer-readable media can include random access memories, read-only memories, hard drives, data cartridges, magnetic tapes, floppy diskettes, flash memory drives, optical data storage devices, compact-disc read-only memories, and other appropriate computer memories and data storage devices. In an illustrative embodiment, some or all of the software components may reside on a single server computer or on any combination of separate server computers. As one skilled in the art can appreciate, a computer program product implementing an embodiment disclosed herein may comprise one or more non-transitory computer readable media storing computer instructions translatable by one or more processors in a computing environment.

A "processor" includes any, hardware system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real-time," "offline," in a "batch mode," etc. Portions of processing can be performed at different times and at different locations, by different (or the same) processing systems.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, product, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein and throughout the claims that follow, the meaning of "in" includes "in" and "on" unless the context clearly dictates otherwise.

It will be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/Figures should be considered only as exemplary, and not limiting, unless otherwise specifically noted.

What is claimed is:

1. A method for real time medical communication, comprising:
   a server computer creating fragments from real time medical data received over a network and stored in rows and columns of a database, the fragments created based at least in part on one or more fragment definitions, the fragments comprising events of interest for medical alerts;
   the server computer analyzing the fragments relative to medical criteria for alert generation;
   according to the analyzing, the server computer generating one or more medical alerts that satisfy the medical criteria for alert generation;
   the server computer determining, for each generated medical alert and based on notification criteria, whether a corresponding notification is to be sent; and
   the server computer sending notifications of generated medical alerts to user devices associated with a plurality of users.

2. The method according to claim 1, wherein the medical criteria for alert generation are patient-specific and are dynamically configurable by the plurality of users via the user devices.

3. The method according to claim 1, wherein each generated medical alert is associated with a fragment definition and a configuration rule.

4. The method according to claim 1, further comprising:
   when a notification of a generated medical alert is to be sent, the server computer applying one or more routing filters.

5. The method according to claim 1, further comprising:
   when a notification of a generated medical alert is not to be sent, the server computer storing or discarding the generated medical alert.

6. The method according to claim 1, further comprising:
   the server computer generating a medical alert at least partially from the fragments.

7. The method according to claim 1, further comprising:
   the server computer sending a notification of a generated medical alert to at least one user device associated with a single user or to a plurality of user devices associated with a group of users.

8. A system for real time medical communication, comprising:
   at least one processor;
   at least one non-transitory computer readable medium;
   stored instructions embodied on the at least one non-transitory computer readable medium and translatable by the at least one processor to perform:
      creating fragments from real time medical data received over a network and stored in rows and columns of a database, the fragments created based at least in part on one or more fragment definitions, the fragments comprising events of interest for medical alerts;
      analyzing the fragments relative to medical criteria for alert generation;
      according to the analyzing, generating one or more medical alerts that satisfy the medical criteria for alert generation;
      determining, for each generated medical alert and based on notification criteria, whether a corresponding notification is to be sent; and sending notifications of generated medical alerts to user devices associated with a plurality of users.

9. The system of claim 8, wherein the medical criteria for alert generation are patient-specific and are dynamically configurable by the plurality of users via the user devices.

10. The system of claim 8, wherein each generated medical alert is associated with a fragment definition and a configuration rule.

11. The system of claim 8, wherein the stored instructions are further translatable by the at least one processor to perform:
when a notification of a generated medical alert is to be sent, applying one or more routing filters.

12. The system of claim 8, wherein the stored instructions are further translatable by the at least one processor to perform:
when a notification of a generated medical alert is not to be sent, storing or discarding the generated medical alert.

13. The system of claim 8, wherein the stored instructions are further translatable by the at least one processor to perform:
generating a medical alert at least partially from the fragments.

14. The system of claim 8, wherein the stored instructions are further translatable by the at least one processor to perform:
sending a notification of a generated medical alert to at least one user device associated with a single user or to a plurality of user devices associated with a group of users.

15. A computer program product for real time medical communication, the computer program product comprising at least one non-transitory computer readable medium storing instructions translatable by at least one processor to perform:
creating fragments from real time medical data received over a network and stored in rows and columns of a database, the fragments created based at least in part on one or more fragment definitions, the fragments comprising events of interest for medical alerts;
analyzing the fragments relative to medical criteria for alert generation;
according to the analyzing, generating one or more medical alerts that satisfy the medical criteria for alert generation;
determining, for each generated medical alert and based on notification criteria, whether a corresponding notification is to be sent; and
sending notifications of generated medical alerts to user devices associated with a plurality of users.

16. The computer program product of claim 15, wherein the medical criteria for alert generation are patient-specific and are dynamically configurable by the plurality of users via the user devices.

17. The computer program product of claim 15, wherein each generated medical alert is associated with a fragment definition and a configuration rule.

18. The computer program product of claim 15, wherein the instructions are further translatable by the at least one processor to perform:
when a notification of a generated medical alert is to be sent, applying one or more routing filters.

19. The computer program product of claim 15, wherein the instructions are further translatable by the at least one processor to perform:
when a notification of a generated medical alert is not to be sent, storing or discarding the generated medical alert.

20. The computer program product of claim 15, wherein the instructions are further translatable by the at least one processor to perform:
generating a medical alert at least partially from the fragments.

21. The computer program product of claim 15, wherein the instructions are further translatable by the at least one processor to perform:
sending a notification of a generated medical alert to at least one user device associated with a single user or to a plurality of user devices associated with a group of users.

* * * * *